United States Patent
Miyoshi

(10) Patent No.: US 9,014,782 B2
(45) Date of Patent: *Apr. 21, 2015

(54) MAGNETIC RESONANCE IMAGING APPARATUS

(75) Inventor: Mitsuharu Miyoshi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 919 days.

This patent is subject to a terminal disclaimer.

(21) Appl. No.: 11/612,614

(22) Filed: Dec. 19, 2006

(65) Prior Publication Data

US 2007/0167733 A1    Jul. 19, 2007

(30) Foreign Application Priority Data

Dec. 22, 2005  (JP) ................................. 2005-370595
Sep. 7, 2006   (JP) ................................. 2006-243203

(51) Int. Cl.
*A61B 5/05*     (2006.01)
*G01R 33/563*   (2006.01)
*A61B 5/055*    (2006.01)
*G01R 33/483*   (2006.01)

(52) U.S. Cl.
CPC ...... *G01R 33/56308* (2013.01); *G01R 33/5635* (2013.01); *A61B 5/055* (2013.01); *G01R 33/4838* (2013.01)

(58) Field of Classification Search
USPC .................................................. 600/407, 419
See application file for complete search history.

(56) References Cited

U.S. PATENT DOCUMENTS

| 4,795,978 | A | | 1/1989 | Zur et al. |
| 5,285,158 | A | * | 2/1994 | Mistretta et al. ............... 324/309 |
| 5,548,216 | A | * | 8/1996 | Dumoulin et al. ............ 324/309 |
| 5,860,921 | A | | 1/1999 | Ma et al. |
| 6,078,176 | A | * | 6/2000 | McKinnon .................... 324/309 |
| 6,295,465 | B1 | | 9/2001 | Simonetti |
| 6,486,668 | B1 | | 11/2002 | Ma |

(Continued)

FOREIGN PATENT DOCUMENTS

JP    06047014    2/1994
JP    09266894    10/1997

(Continued)

OTHER PUBLICATIONS

Japanese Office Action; Application No. JP2006243203; dated Sep. 27, 2011; pp. 4.

(Continued)

*Primary Examiner* — Long V Le
*Assistant Examiner* — Ellsworth Weatherby
(74) *Attorney, Agent, or Firm* — Armstrong Teasdale LLP

(57) ABSTRACT

Versatility and the quality of images are to be improved. As preparation pulses, a first RF pulse to flip along the yz plane spins oriented in a magnetostatic field direction in a subject; a velocity encoding gradient pulse which, in spins flipped by that first RF pulse, mutually shifts the phase of spins in a static state and the phase of spins in a moving state; and a second RF pulse to flip along the yz plane spins whose phase has been shifted by the velocity encoding gradient pulse are successively transmitted. After that, a killer pulse is transmitted to extinguish the transverse magnetizations of the spins flipped by the second RF pulse.

14 Claims, 20 Drawing Sheets

(56) References Cited

U.S. PATENT DOCUMENTS

| | | |
|---|---|---|
| 6,587,708 B2 | 7/2003 | Venkatesan et al. |
| 7,541,809 B2 * | 6/2009 | Miyoshi .................. 324/309 |
| 2004/0059213 A1 * | 3/2004 | Kassai et al. ................. 600/410 |
| 2004/0162483 A1 | 8/2004 | Kimura |
| 2006/0020198 A1 * | 1/2006 | Riederer et al. ............. 600/410 |
| 2006/0080044 A1 | 4/2006 | Ropele |

FOREIGN PATENT DOCUMENTS

| | | |
|---|---|---|
| JP | 11253417 | 9/1999 |
| JP | 2000005144 | 1/2000 |

OTHER PUBLICATIONS

German Patent Office, Translation of Office Action for Patent No. 10 2006 060 490.3-54, Jan. 4, 2011, 4 pages, Germany.

* cited by examiner

MAGNETIC RESONANCE IMAGING APPARATUS

CROSS REFERENCE TO RELATED APPLICATIONS

This application claims the benefit of Japanese Application No. 2005-370595 filed Dec. 22, 2005 and Japanese Application No. 2006-243203 filed Sep. 7, 2006.

BACKGROUND OF THE INVENTION

The present invention relates to a magnetic resonance imaging apparatus, and to a magnetic resonance imaging apparatus which transmits RF pulses to a subject in a magnetostatic space, performs an imaging sequence in which magnetic resonance signals generated by transmitting gradient pulses to the subject to which the RF pulses are transmitted are obtained as imaging data, and an image of the subject is generated on the basis of the imaging data obtained by the performance of the imaging sequence.

Magnetic resonance imaging (MRI) apparatuses are used in many different fields including medical and industrial purposes.

A magnetic resonance imaging apparatus excites spins of protons in a subject in a magnetostatic space by a nuclear magnetic resonance (NMR) phenomenon by irradiating the subject with an electromagnetic wave, and performs scanning to obtain magnetic resonance (MR) signals generated by the excited spins. And an image regarding the subject is generated from the magnetic resonance signals obtained by the scanning as raw data.

With a magnetic resonance imaging apparatus, blood vessel photography known as MRA (MR angiography) is performed for instance. As an MRA imaging method using no contrast medium, FBI (fresh blood imaging) is known (see Patent Document 1 for example). Other such methods include imaging methods utilizing the time of flight (TOF) effect or the phase contrast (PC) effect.

[Patent Document 1] Unexamined Japanese Patent Publication No. 2000-5144

By the FBI method, images are created regarding the imaging area in each of the diastole and the systole of the heart. And MRA images regarding the imaging area are obtained on the basis of the difference values between these images. Here, the signal intensity from the artery is lower in the systole because the blood stream velocity in the artery is faster and the signal intensity from the artery is higher in the diastole because the blood stream velocity in the artery is slower, with the result that the MRA images created on the basis of the difference values become more contrasty.

However, since a plurality of images are picked up at a plurality of timings and the MRA images are created by using the difference values between the images by the FBI method, if the subject moves its body in the course of imaging, body motion artifacts will arise significantly, and images may be blurred by T2 attenuation in the direction of phase encoding, possibly posing a difficulty to improve the quality of images.

In other imaging methods, in addition to the problem noted above, the imaging area is restricted, resulting in poor versatility.

These troubles would become especially conspicuous for the trunk and the lower thighs of the subject, because the artery and the vein run substantially parallel to each other and the T1 values and T2 values of the artery and the vein are close to each other.

SUMMARY OF THE INVENTION

Therefore, an object of the present invention is to provide a magnetic resonance imaging apparatus which is highly versatile and can improve the quality of images.

In order to achieve the object state above, a magnetic resonance imaging apparatus which transmits RF pulses to a subject in a magnetostatic space, executes an imaging sequence in which magnetic resonance signals generated in the subject are obtained as imaging data by transmitting gradient pulses to the subject to which the RF pulses have been transmitted, and generates an image of the subject on the basis of the imaging data obtained by the execution of the imaging sequence, the magnetic resonance imaging apparatus including a scanning unit which executes the imaging sequence and, before the execution of the imaging sequence, executes a preparation sequence in which preparation pulses are transmitted to the subject, wherein the scanning unit, after successively transmitting to the subject as the preparation pulses, a first RF pulse to flip spins oriented in a magnetostatic direction in the subject along a first plane including the magnetostatic direction and a first direction orthogonal to the magnetostatic direction, a velocity encoding gradient pulse to mutually shift, in the spins flipped by the first RF pulse, the phase of spins of a first velocity and the phase of spin of a second velocity different from the first velocity, and a second RF pulse to flip along the first plane the spins whose phase having shifted by the velocity encoding gradient pulse, further transmits a killer pulse to generate a gradient magnetic field which extinguishes the transverse magnetization of said spins flipped by said second RF pulse.

In order to achieve the object state above, a magnetic resonance imaging apparatus according to the invention executes an imaging sequence in which magnetic resonance signals generated in a subject are obtained as imaging data by transmitting RF pulses to the subject in a magnetostatic space, generates an image of the subject on the basis of the imaging data obtained by executing the imaging sequence, and includes a scanning unit which executes the imaging sequence and executes before the execution of the imaging sequence a preparation sequence in which preparation pulses are so transmitted as to vary the signal intensity of the imaging data according to the velocity of a fluid flowing in the subject, wherein the scanning unit executes the preparation sequence in the systole in heart beating of the subject and executes the imaging sequence in the diastole of the heart beating.

According to the present invention, it is possible to provide a magnetic resonance imaging apparatus which is highly versatile and can improve the quality of images.

Further objects and advantages of the present invention will be apparent from the following description of the preferred embodiments of the invention as illustrated in the accompanying drawings.

BRIEF DESCRIPTION OF THE DRAWINGS

FIGS. 4A1, 4A2, 4A3, 4A4, 4A5, 4B1, 4B2, 4B3, 4B4, and 4B5 are vector diagrams showing the behavior of the spins of the subject SU when the preparation sequence PS is executed in Mode for Implementation 1 pertaining to the invention.

FIG. 5 is a pulse sequence chart of the imaging sequence IS in Mode for Implementation 1 pertaining to the invention.

FIGS. 7A1, 7A2, 7A3, 7A4, 7A5, 7B1, 7B2, 7B3, 7B4, and 7B5 are vector diagrams showing the behavior of the spins of the subject SU when the preparation sequence PS is executed in Mode for Implementation 1 pertaining to the invention.

FIGS. 8A1, 8A2, 8A3, 8A4, 8A5, 8B1, 8B2, 8B3, 8B4, and 8B5 are vector diagrams showing the behavior of the spins of the subject SU when the preparation sequence PS is executed in Mode for Implementation 1 pertaining to the invention, a vector diagram to be shown next to FIG. 7.

DETAILED DESCRIPTION OF THE INVENTION

Mode for Implementation 1

Mode for Implementation 1 pertaining to the present invention will be described.

(Hardware Configuration)

Figure 1:
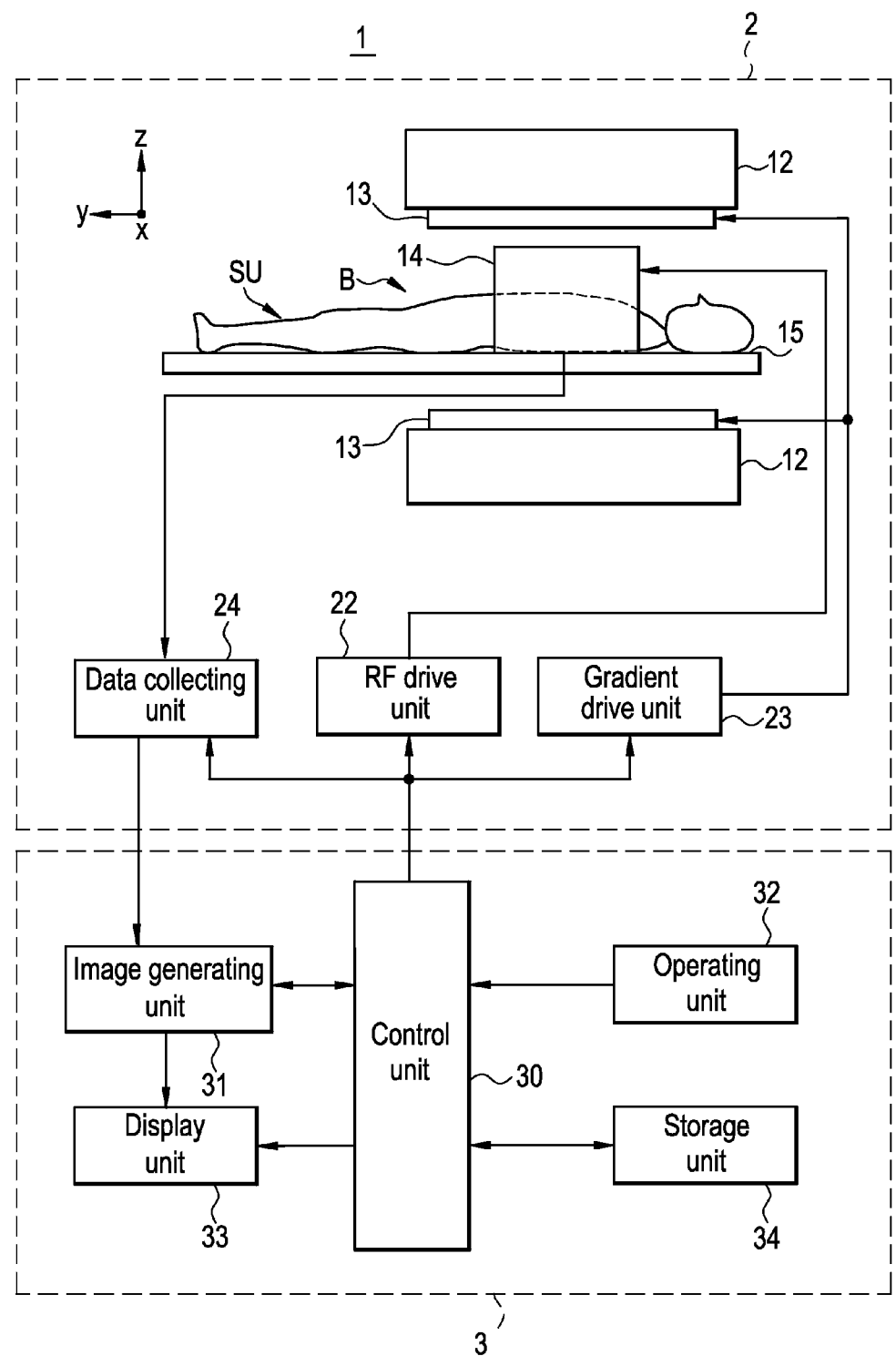
FIG. 1 is a configurational diagram showing the configuration of the magnetic resonance imaging apparatus 1 in a mode for implementation pertaining to the present invention.

FIG. 1 is a configurational diagram showing the configuration of a magnetic resonance imaging apparatus 1 in Mode for Implementation 1 pertaining to the invention.

As shown in FIG. 1, the magnetic resonance imaging apparatus 1 in this mode for implementation has a scanning unit 2 and an operation console unit 3.

The scanning unit 2 will be described.

The scanning unit 2 has, as shown in FIG. 1, has a magnetostatic magnet unit 12, a gradient coil unit 13, an RF coil unit 14, a cradle 15, an RF drive unit 22, a gradient drive unit 23 and a data collecting unit 24. The scanning unit 2 transmits RF pulses to a subject SU so as to excite spinning of the subject SU in an imaging space B in which a magnetostatic field is formed, and performs an imaging sequence IS in which magnetic resonance signals generated in the subject SU by the transmission of gradient pulses to the subject SU to which the RF pulses have been transmitted are obtained as imaging data. The scanning unit 2, besides performing the imaging sequence IS, performs a preparation sequence PS in which preparation pulses are transmitted to the subject SU before this imaging sequence IS.

Whereas details will be described afterwards, the scanning unit 2 successively transmits, as preparation pulses for this preparation sequence PS, a first RF pulse which flips spins oriented in the magnetostatic direction z in the subject SU along a yz plane containing that magnetostatic direction z and a y direction orthogonally crossing that magnetostatic direction z; a velocity encoding gradient pulse which mutually shifts, in the spins flipped by that first RF pulse, the phase of the spin of a first velocity and the phase of the spin of a second velocity different from that first velocity; and a second RF pulse which flips along the yz plane the spin whose phase has been shifted by that velocity encoding gradient pulse. Here, transmission is so performed to the subject SU successively as to equalize a first time interval between the central time point of the duration of first RF pulse transmission and the central time point of the duration of velocity encoding gradient pulse transmission and a second time interval between the central time point of the duration of velocity encoding gradient pulse transmission and the central time point of the duration of second RF pulse transmission. It further transmits a killer pulse which generates a gradient magnetic field to extinguish the transverse magnetization of the spin flipped by the second RF pulse. Thus, in the preparation sequence in this mode for implementation, preparation pulses are so transmitted as to vary the signal intensity of the imaging data obtained in the imaging sequence IS according to the velocity of a fluid flowing in the subject.

After that, the scanning unit 2 executes the imaging sequence IS by an SSFP (steady state free procession) type imaging method known as FIESTA, True FISP or Balanced TFE. More specifically, the scanning unit 2 transmits, as the imaging sequence IS, RF pulses to the subject SU in such a time of repeat that the longitudinal magnetization and the transverse magnetization of spins take on a steady state in the subject SU. Along with this, it transmits as gradient pulses to the subject SU within the time of repeat a slice selecting gradient pulse by which a slice of the subject SU excited by that RF pulse is selected as the imaging area, a frequency encoding gradient pulse by which magnetic resonance signals generated in the slice excited by that RF pulse are frequency-encoded, and a phase encoding gradient pulse by which magnetic resonance signals generated in the slice excited by that RF pulse are phase-encoded. Here, each of the slice selecting gradient pulse, the phase encoding gradient pulse and the frequency encoding gradient pulse is so transmitted to the subject SU as to reduce the time-integrated value within the time of repeat to zero.

The constituent elements of the scanning unit 2 will be described in due order.

The magnetostatic magnet unit 12 is configured of, for instance, a pair of permanent magnets, and forms a magnetostatic field in an imaging space B in which the subject SU is accommodated. Here, the magnetostatic magnet unit 12 so forms a magnetostatic field as to orient the magnetostatic direction along a direction z normal to the body axis direction of the subject SU. Incidentally, the magnetostatic magnet unit 12 may be configured of superconducting magnets.

The gradient coil unit 13 forms a gradient magnetic field in the imaging space B in which a magnetostatic field is formed, and adds spatial position information to the magnetic resonance signals received by the RF coil unit 14. Here, the gradient coil unit 13 consists of three lines to match the mutually orthogonal three axial directions including the z direction along the magnetostatic direction, the x direction and the y direction. Regarding these, a gradient magnetic field is formed by transmitting gradient pulses in each of the frequency encoding direction, the phase encoding direction and the slice selecting direction according to the imaging conditions. More specifically, as the gradient coil unit 13 applies a gradient magnetic field in the slice selecting direction of the subject SU, and the RF coil unit 14 transmits RF pulses, the excited slice of the subject SU is selected. Further, the gradient coil unit 13 applies a gradient magnetic field in the phase encoding direction of the subject SU, and phase-encodes the magnetic resonance signals from the slice excited by the RF pulses. And the gradient coil unit 13 applies the gradient magnetic field in the frequency encoding direction of the subject SU, and frequency-encodes the magnetic resonance signals from the slice excited by the RF pulses.

The RF coil unit 14, as shown in FIG. 1, is so arranged as to surround the imaging area of the subject SU. The RF coil unit 14 transmits RF pulses, which constitute an electromagnetic wave to the subject SU in the imaging space B in which a magnetostatic field is formed by the magnetostatic magnet unit 12 to form a high frequency magnetic field, excites the spinning of protons in the imaging area of the subject SU. And the RF coil unit 14 receives as magnetic resonance signals the electromagnetic wave generated from the excited protons in the subject SU.

The cradle 15 has a table on which the subject SU is to be mounted. The cradle unit 15 moves between the inside and the outside of the imaging space B in accordance with a control signal from a control unit 30.

The RF drive unit 22 drives the RF coil unit 14 to have RF pulses transmitted into the imaging space B to form a high frequency magnetic field. The RF drive unit 22, after modulating signals from an RF oscillator into signals of a prescribed timing and a prescribed envelope by using a gate modulator in accordance with a control signal from the control unit 30, outputs the signals modulated by that gate modulator to the RF coil unit 14 with an RF power amplifier to have RF pulses transmitted.

The gradient drive unit 23 drives the gradient coil unit 13 by applying gradient pulses in accordance with a control signal from the control unit 30, and thereby generates a gradient magnetic field in the imaging space B in which a magnetostatic field is formed. The gradient drive unit 23 has three lines of drive circuits (not shown) to match the three lines of the gradient coil unit 13.

The data collecting unit 24, in accordance with a control signal from the control unit 30, collects magnetic resonance signals received by the RF coil unit 14. Here, in the data collecting unit 24, the magnetic resonance signals received by the RF coil unit 14 a phase detector performs phase detection with the output of the RF oscillator of the RF drive unit 22 as the reference signal. After that, the magnetic resonance signals, which are analog signals, are converted into digital signals by using an A/D converter, and outputted.

The operation console unit 3 will be described.

The operation console unit 3, as shown in FIG. 1, has the control unit 30, an image generating unit 31, an operating unit 32, a display unit 33 and a storage unit 34.

The constituent elements of the operation console unit 3 will be described in due order.

The control unit 30, having a computer and a program which causes the computer to perform prescribed data processing, controls various units. Here the control unit 30, to which operation data from the operating unit 32 are inputted, outputs a control signal to each of the RF drive unit 22, the gradient drive unit 23 and the data collecting unit 24 on the basis of those inputted from the operating unit 32 to have prescribed scanning executed, and thereby performs control. And along with this, it outputs a control signal to each of the image generating unit 31, the display unit 33 and the storage unit 34, and thereby performs control.

The image generating unit 31, having a computer and a program which causes the computer to perform prescribed data processing, generates an image in accordance with a control signal from the control unit 30. Here, the image generating unit 31, using as raw data the magnetic resonance signals obtained by the execution of scanning by the scanning unit 2, reconstructs an image regarding the subject SU. And the image generating unit 31 outputs that generated image to the display unit 33.

The operating unit 32 is configured of operating devices including a keyboard and a pointing device. The operating unit 32, to which the operator inputs operation data, outputs those operation data to the control unit 30.

The display unit 33, configured of a display device such as a CRT, displays an image on the display screen in accordance with a control signal from the control unit 30. For instance, the display unit 33 displays a plurality of images regarding an input item whose operation data are inputted by the operator to the operating unit 32. Also, the display unit 33 receives from the image generating unit 31 data regarding an image of the subject SU generated in accordance with magnetic resonance signals from the subject SU, and displays that image on the display screen.

The storage unit 34, configured of a memory, stores various sets of data. The storage unit 34 is accessed as required by the control unit 30 for the data stored therein.

(Actions)

The actions which take place when picking up an image of the subject SU by using the magnetic resonance imaging apparatus 1 in the above-described mode for implementing the present invention will be described hereinafter.

Figure 2:
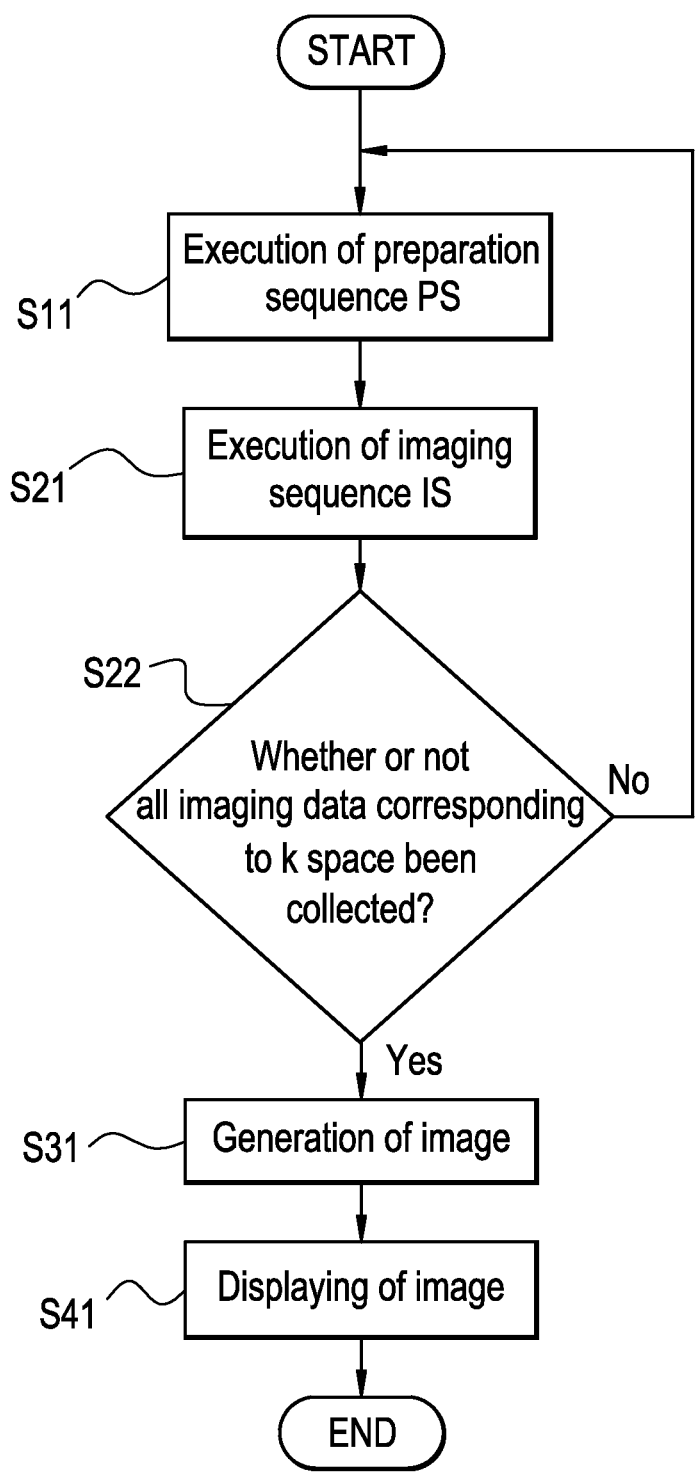
FIG. 2 is a flow chart showing the actions which take place when picking up an image of the subject SU in Mode for Implementation 1 pertaining to the invention.

FIG. 2 is a flow chart showing the actions which take place when picking up an image of the subject SU in Mode for Implementation 1 of the invention.

First, as charted in FIG. 2, the preparation sequence PS is executed (S11).

Here, the preparation sequence PS is executed by the scanning unit 2.

Figure 3:
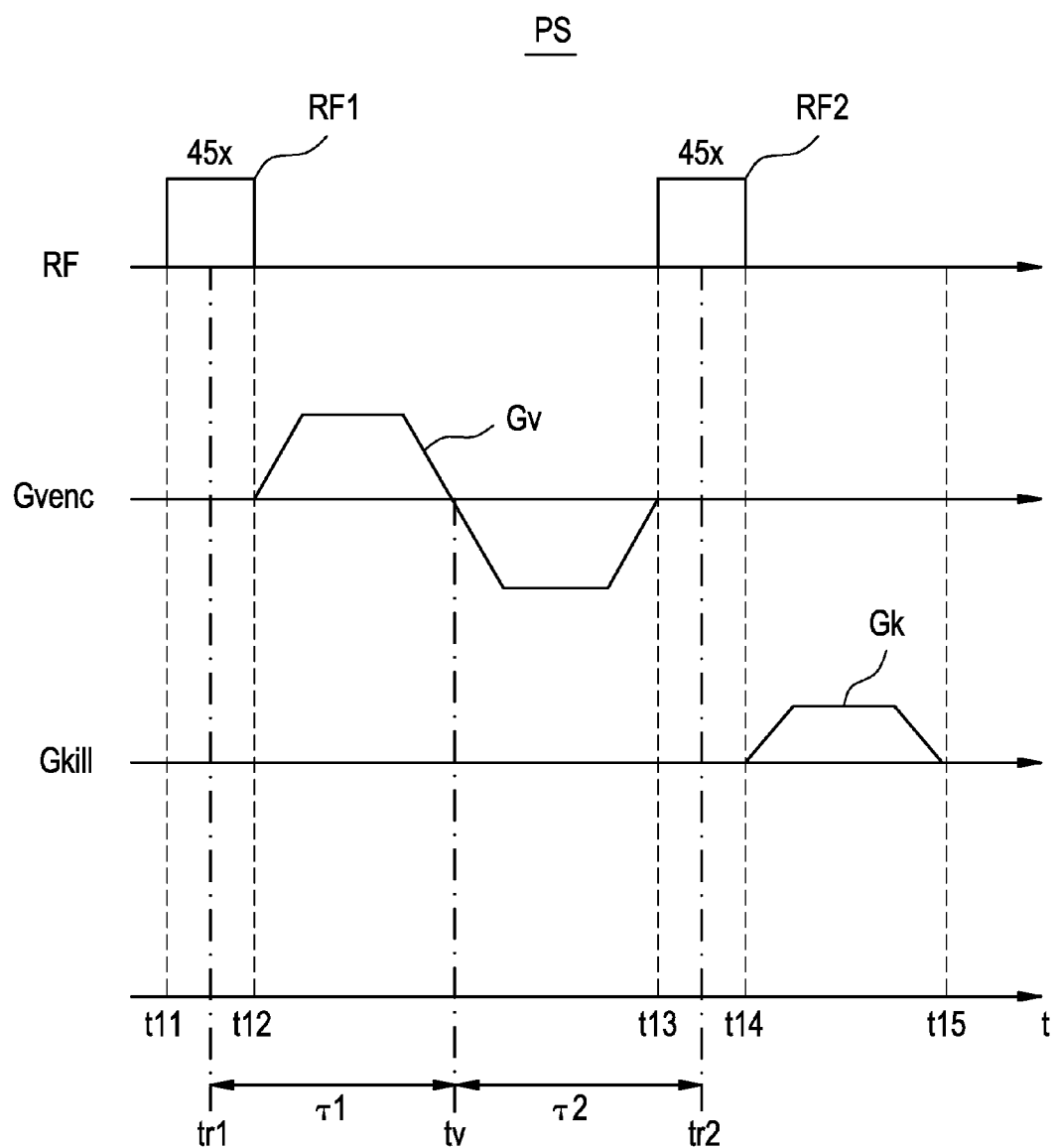
FIG. 3 is a pulse sequence chart showing the preparation sequence PS in Mode for Implementation 1 pertaining to the invention.

FIG. 3 is a pulse sequence chart showing the preparation sequence PS in Mode for Implementation 1 of the invention.

In FIG. 3, RF denotes the time axis of transmitting RF pulses; Gvenc, the time axis of transmitting velocity encoding pulses; and Gkill, the time axis of transmitting killer pulses, for each of which the horizontal axis represents the time t and the vertical axis, the pulse intensity. Here, Gvenc and Gkill are the time axes of transmitting gradient pulses, each being a time axis in at least one of the slice selecting direction, the phase encoding direction and the frequency encoding direction.

Figure 4:
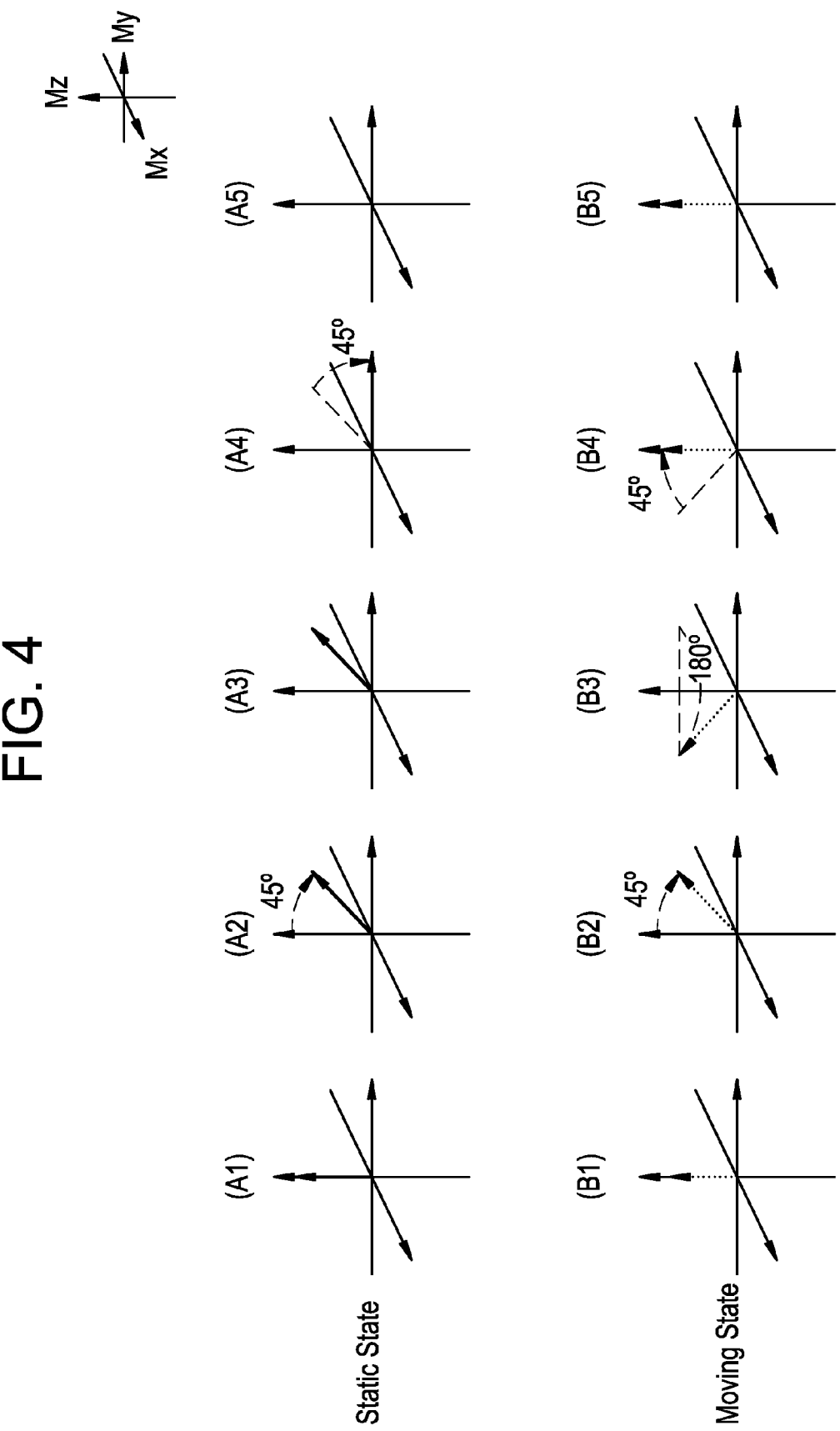

FIG. 4 is a vector diagram showing the behavior of the spins of the subject SU when the preparation sequence PS is executed in Mode for Implementation 1 of the invention.

In FIG. 4, (A1), (A2), (A3), (A4) and (A5) refer to the behavior of the subject SU regarding a spin S1 at a first velocity V1 sequentially in a time series. Here is shown the behavior regarding the spin S1 where the first velocity V1 is zero, namely in a static state. On the other hand in FIG. 4, (B1), (B2), (B3), (B4) and (B5) refer to the behavior of the subject SU regarding a spin S2 moving at a second velocity V2, faster than the first velocity V1, sequentially in a time series.

Further in FIG. 4, (A1) and (B1) show the state manifested by the spins S1 and S2 at a first time point t11 in the pulse sequence chart shown in FIG. 3. (A2) and (B2) show the state manifested by the spins S1 and S2 at a second time point t12 in the pulse sequence chart shown in FIG. 3. (A3) and (B3) show the state manifested by the spins S1 and S2 at a third time point t13 in the pulse sequence chart shown in FIG. 3. (A4) and (B4) show the state manifested by the spins S1 and S2 at a fourth time point t14 in the pulse sequence chart shown in FIG. 3. (A5) and (B5) show the state manifested by the spins S1 and S2 at a fifth time point t15 in the pulse sequence chart shown in FIG. 3.

As shown in FIG. 3, when executing the pulse sequence PS, the scanning unit 2 successively transmits to the subject SU a first RF pulse RF1, a velocity encoding gradient pulse Gv, a second RF pulse RF2 and a killer pulse Gk as preparation pulses.

Here, as shown in FIG. 3, the first RF pulse RF1, the velocity encoding gradient pulse Gv and the second RF pulse RF2 are so transmitted successively to the subject SU as to equalize a first time interval τ1 between the central time point tr1 of the time during which the first RF pulse RF1 is transmitted and the central time point tv of the time during which the velocity encoding gradient pulse Gv is transmitted and a second time interval τ2 between the central time point tv of the time during which the velocity encoding gradient pulse Gv is transmitted and the central time point tr2 of the time during which the second RF pulse RF2 is transmitted. In other words, between the transmission of the first RF pulse RF1 and that of the second RF pulse RFw, the velocity encoding gradient pulse Gv is transmitted. And after that, the killer pulse Gk is further transmitted.

The preparation pulses in the preparation sequence PS will be described in due order.

First, as shown in FIG. 3, the first RF pulse RF1 is transmitted to the subject SU.

Here, as shown in FIG. 3, from the first time point t11 until the second time point t12, the scanning unit 2 transmits the first RF pulse RF1, which is a rectangular pulse. In this mode for implementation, as indicated by FIG. 4 (A1) and FIG. 4 (B1), the magnetization vector is oriented in the magnetostatic direction z in the subject SU, and the scanning unit 2 transmits the first RF pulse RF1 to the spins S1 and S2 of protons differing in velocity from each other. As indicated by FIG. 4 (A2) and FIG. 4 (B2), the magnetization vector of these spins S1 and S2 is so flipped as to be along the yz plane.

More specifically, as indicated by FIG. 4 (A1) and FIG. 4 (B1), the first RF pulse RF1 of which the flip angle is 45° and the phase is in the x direction is transmitted to the spins S1 and S2 of which the longitudinal magnetization is M0 and the transverse magnetization is zero and, as indicated by FIG. 4 (A2) and FIG. 4 (B2), the magnetization vector attributable to the spins S1 and S2 is inclined on the yz plane from the 0° direction to the 45° direction.

Next, as shown in FIG. 3, the velocity encoding gradient pulse Gv is transmitted to the subject SU.

Here, as shown in FIG. 3, from the second time point t12 until the third time point t13, the scanning unit 2 transmits the velocity encoding gradient pulse Gv. In this mode for implementation, the scanning unit 2 transmits this velocity encoding gradient pulse Gv as a bipolar pulse inverse in polarity on the time axis with respect to the central time point tv at which the velocity encoding gradient pulse Gv is transmitted and the same in time-integrated value. As indicated by FIG. 4 (A3) and FIG. 4 (B3), in the spins S1 and S2 flipped by the first RF pulse RF1, the phase of the spin S1 of the first velocity and the phase of the spin S2 of the second velocity V2 faster than that first velocity V1 are mutually shifted.

More specifically, as indicated by FIG. 4 (A3) and FIG. 4 (B3), the velocity encoding gradient pulse Gv is so transmitted as to mutually shift the phase of the spin S1 of protons whose first velocity V1 and which is in a static state and the phase of the spin S2 of the phase of the spin S2 of protons which are in a moving state of moving at the second velocity V2 faster than the first velocity V1 by 180°. In other words, regarding the spin S1 of protons in the static state, as indicated by FIG. 4 (A3), the transmission of the velocity encoding gradient pulse Gv does not change the direction of the magnetization vector of the spin S1. On the other hand, regarding the spin S2 of protons in the moving state, as indicated by FIG. 4 (B3), the transmission of the velocity encoding gradient pulse Gv turns the magnetization vector of the spin S2 at an angle of 180° along the xy plane, varying it from the 45° direction on the xy plane to the −45° direction.

Next, as shown in FIG. 3, the second RF pulse RF2 is transmitted to the subject SU.

Here, as shown in FIG. 3, the scanning unit 2 transmits the second RF pulse RF2, which is a rectangular pulse, from the third time point t13 until the fourth time point t14. As indicated by FIG. 4 (A4) and FIG. 4 (B4), the spins S1 and S2 whose phases have been shifted by the velocity encoding gradient pulse Gv are flipped along the yz plane.

More specifically, the second RF pulse RF2 of which the flip angle is 45° and the phase is in the x direction is transmitted to incline the magnetization vector of the spin S1 in a static state from the 45° direction to the 90° direction on the yz plane as indicated by FIG. 4 (A4) and incline the magnetization vector of the spin S2 in a moving state from the −45° direction to the 0° direction as indicated by FIG. 4 (B4).

Incidentally, where the angle in which the velocity encoding gradient pulse Gv shifts the phase is θ, the longitudinal magnetization Mz and the transverse magnetization Mxy are respectively represented by Mathematical Expression (1) and Mathematical Expression (2) below.

[Mathematical Expression 1]

$$Mz = \frac{(1-\cos\theta)}{2} \quad (1)$$

[Mathematical Expression 2]

$$Mxy = \sqrt{1 - \frac{(1-\cos\theta)^2}{4}} \quad (2)$$

Next, as shown in FIG. 3, the killer pulse Gk is transmitted to the subject SU.

Here, as shown in FIG. 3, the scanning unit 2 transmits the killer pulse Gk from the fourth time point t14 until the fifth time point t15. As indicated by FIG. 4 (A5) and FIG. 4 (B5), the transverse magnetization of the spins S1 and S2 flipped by the second RF pulse RF2 is extinguished.

In other words, by transmitting the killer pulse Gk as indicated by FIG. 4 (A5), the magnetization vector of the spin S1 in a static state oriented in the 90° direction on the yz plane is dispersed in phase and thereby extinguished.

Next, as charted in FIG. 2, the imaging sequence IS is executed (S21).

Here, the scanning unit 2 executes the imaging sequence IS by an SSFP imaging method.

Figure 5:
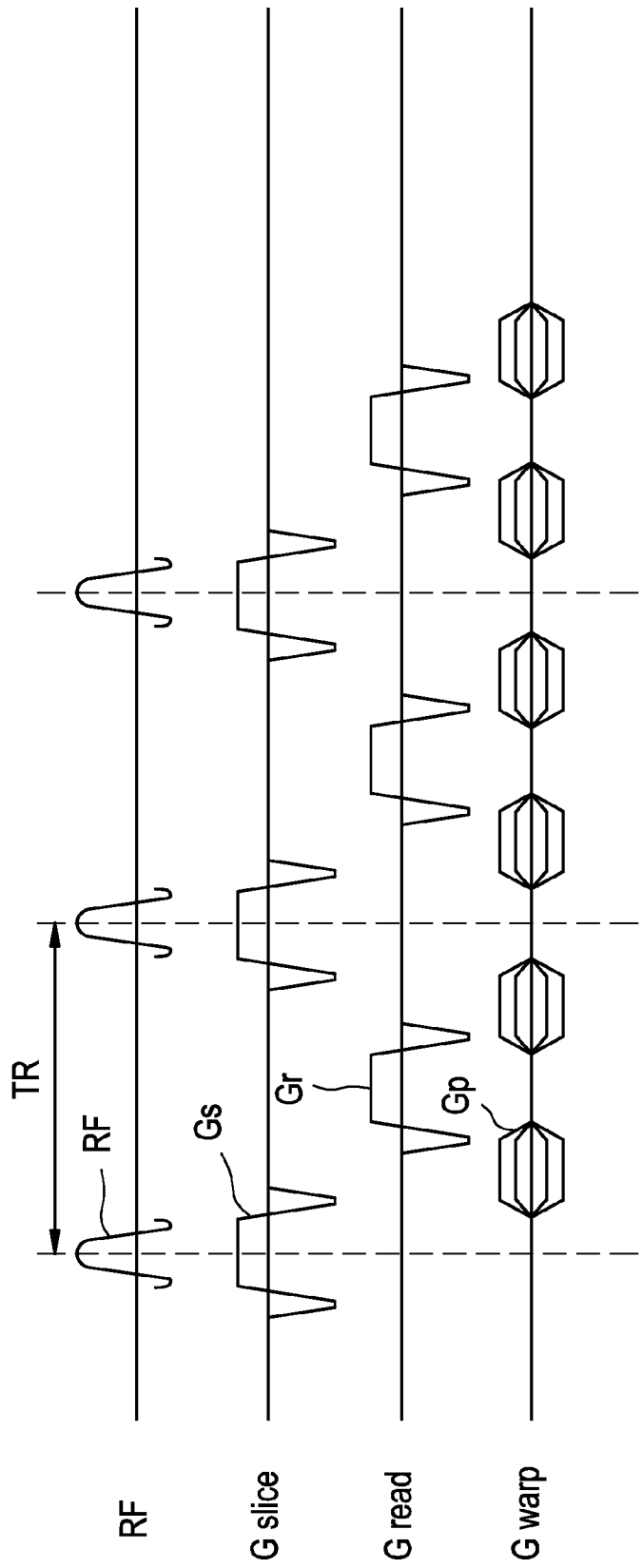

FIG. 5 is a pulse sequence chart of the imaging sequence IS in Mode for Implementation 1 of the present invention.

In FIG. 5, RF denotes the time axis on which RF pulses are transmitted; Gslice, the time axis on which gradient pulses are transmitted in the slice selection encoding direction; Gread, the time axis on which gradient pulses are transmitted in the read-out direction; and Gwarp, the time axis on which gradient pulses are transmitted in the phase encoding direction, for each of which the horizontal axis represents the time t and the vertical axis, the pulse intensity.

As shown in FIG. 5, in executing the imaging sequence IS, RF pulses RF are repeatedly transmitted to the subject SU. Here, the scanning unit 2 transmits RF pulses RF to the subject SU in such a time of repeat TR that the longitudinal magnetization and the transverse magnetization of spins in the subject SU take on a steady state.

And along with this, a slice selecting gradient pulse Gs for selecting the slice of the subject SU excited by those RF pulses RF, a phase encoding gradient pulse Gr for phase-encoding the magnetic resonance signals generated in the slice excited by those RF pulses, and a frequency encoding gradient pulse for frequency-encoding the magnetic resonance signals generated in the slice excited by those RF pulses are transmitted as gradient pulses to the subject SU within the time of repeat TR. Here, the slice selecting gradient pulse, the phase encoding gradient pulse and the frequency encoding gradient pulse are so transmitted to the subject SU as to reduce the time-integrated value within the time of repeat TR to zero. In other words, as shown in FIG. 5, after the magnetic resonance signals are collected as imaging data, the transverse magnetization is rewound within the time of repeat TR and the phase encoded in the gradient magnetic field is reset.

Next, as charted in FIG. 2, it is judged whether or not all the imaging data corresponding to the k space have been collected (S22).

Here, the control unit 30 judges whether or not all the imaging data corresponding to the k space have been collected.

And if all the imaging data corresponding to the k space have not been collected (No), the execution of the preparation sequence PS (S11) and the execution of the imaging sequence IS (S21) are successively carried out again as shown in FIG. 2. Thus, imaging data are collected until the k space is completely filled by repeating the execution of the preparation sequence PS (S11) and the execution of the imaging sequence IS (S21).

On the other hand, if all the imaging data corresponding to the k space have been collected (Yes), an image is generated as charted in FIG. 2 (S31).

Here, with the imaging data obtained by the execution of the imaging sequence IS by the scanning unit 2 being used as raw data, the image generating unit 31 reconstructs an image regarding the subject SU.

In this mode for implementation, as spins in a moving state has a large longitudinal magnetization and there is a great different from the longitudinal magnetization of spins in a static state, there is generated an image in which spins in a moving state are emphasized.

Next, an image is displayed as charted in FIG. 2 (S41).

Here, the display unit 33 receives data regarding an image of the subject SU from the image generating unit 31, and displays that image on the display screen.

As described above, in this mode for implementation, the imaging sequence IS is executed by the scanning unit 2 and, before that imaging sequence IS is executed, the scanning unit 2 also executes the preparation sequence PS in which preparation pulses are transmitted to the subject SU. The scanning unit 2 successively transmits to the subject SU as these preparation pulses the first RF pulse RF1 which flips along the yz plane the spins oriented in the magnetostatic direction z in the subject SU; the velocity encoding gradient pulse Gv which shifts, in those spins flipped by the first RF pulse RF1, the phase of the spin S1 in a static state and the phase of the spin S2 in a moving state; and the second RF pulse RF2 which flips the spins S1 and S2 whose phases have been shifted by the velocity encoding gradient pulse Gv along the yz plane. Here, the first RF pulse RF1, the velocity encoding gradient pulse Gv and the second RF pulse RF2 are so transmitted successively to the subject SU as to equalize the first time interval τ1 between the central time point tr1 of the time during which the first RF pulse RF1 is transmitted and the central time point tv of the time during which the velocity encoding gradient pulse Gv is transmitted and the second time interval τ2 between the central time point tv of the time during which the velocity encoding gradient pulse Gv is transmitted and the central time point tr2 of the time during which the second RF pulse RF2 is transmitted. And after that, it further transmits the killer pulse Gk to extinguish the transverse magnetization of the spin flipped by the second RF pulse.

As a result, in this mode for implementation, an image in which the part moving at a prescribed moving velocity is emphasized in the subject SU can be obtained as described above. Also, since the time during which preparation pulses are applied is short, it can be utilized for various purposes. For instance, since magnetic resonance signals from arteries in which the flow velocity is high, such as the ventral aorta, the iliac artery and the femoral artery can be obtained with higher signal intensities than from veins, cerebrospinal fluid and urine, contrasty images according to the moving velocity can be obtained.

Further in this mode for implementation, since the scanning unit 2 executes the imaging sequence IS by the SSFP type imaging method called FIESTA or otherwise, signals of high signal intensities can be obtained from tissues of a high S/N ratio and a low T2/T1 ratio can be obtained, making it possible to obtain contrasty images according to the moving velocity. While high signal intensities can be obtained from veins, cerebrospinal fluid and urine in this case, by transmitting preparation pulses in this mode for implementation, images regarding arteries of high flow velocities can be obtained with high contrast.

Therefore in this mode for implementation, versatility can be enhanced without having to use a contrast medium, and at the same time the quality of images can be improved.

Mode for Implementation 2

Mode for Implementation 2 pertaining to the present invention will be described.

This mode for implementation differs from the next Mode for Implementation 1 (FIG. 3) in the preparation sequence executed at the time of imaging the subject SU. This mode for implementation is a preparation sequence based on the so-called CPMG (Carr-Purcell-Meiboon-Gukk) method, and is similar to Mode for Implementation 1 except in this respect. For this reason, description of duplicated parts will be dispensed with.

Figure 6:
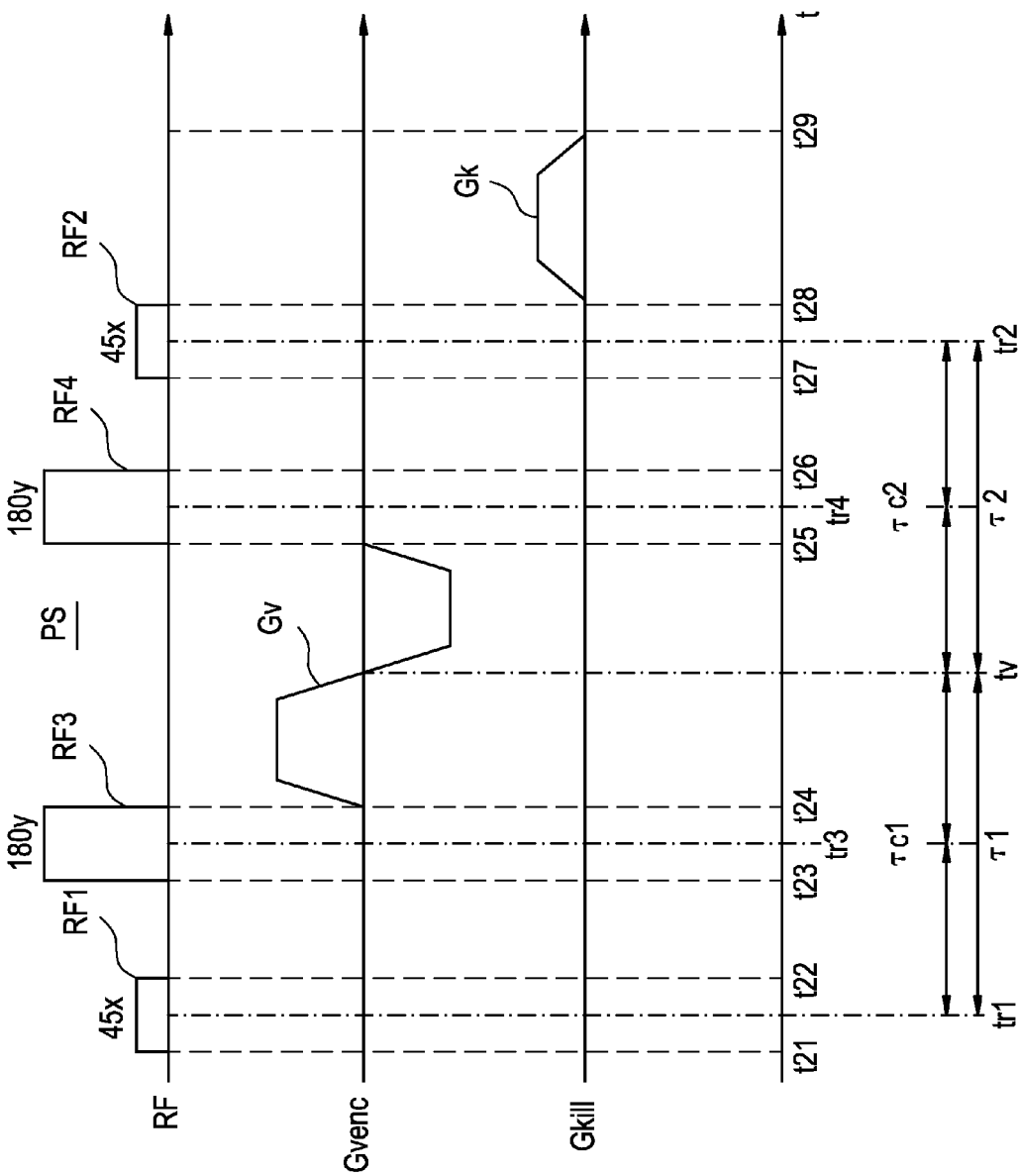
FIG. 6 is a pulse sequence chart showing a preparation sequence PS in Mode for Implementation 2 pertaining to the invention.

FIG. 6 is a pulse sequence chart showing a preparation sequence PS in Mode for Implementation 2 pertaining to the invention.

In FIG. 6, RF denotes the time axis of transmitting RF pulses; Gvenc, the time axis of transmitting velocity encoding pulses; and Gkill, the time axis of transmitting killer pulses, for each of which the horizontal axis represents the time t and the vertical axis, the pulse intensity. Here, Gvenc and Gkill are the time axes of transmitting gradient pulses, each being a time axis in at least one of the slice selecting direction, the phase encoding direction and the frequency encoding direction.

Figure 7:
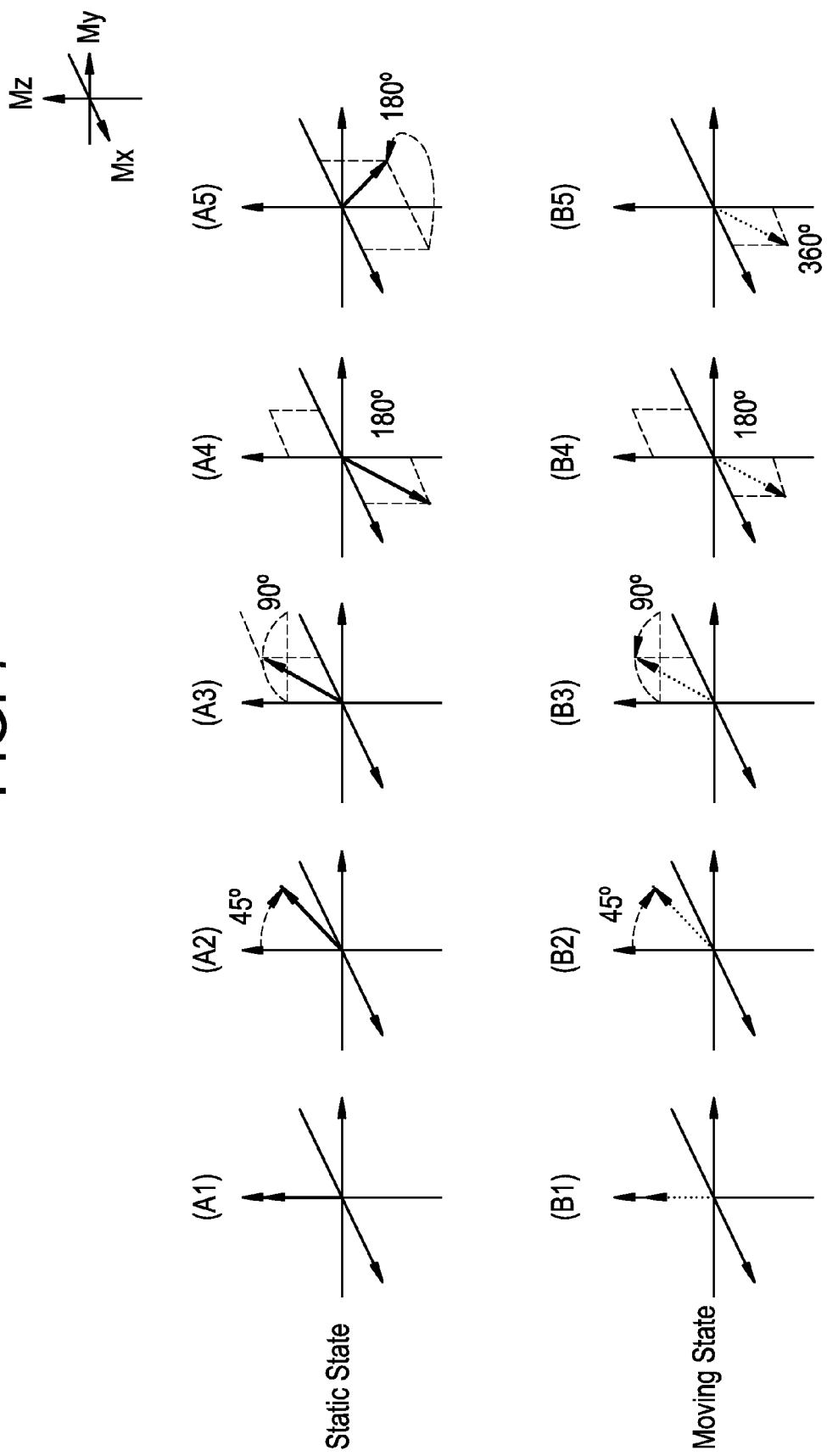

FIG. 7 is a vector diagram showing the behavior of the spins of the subject SU when the preparation sequence PS is executed in Mode for Implementation 1 of the invention. Similarly, FIG. 8 is a vector diagram showing the behavior of the spins of the subject SU when the preparation sequence PS is executed in Mode for Implementation 1 of the invention, a vector diagram to be shown next to FIG. 7.

Figure 8:
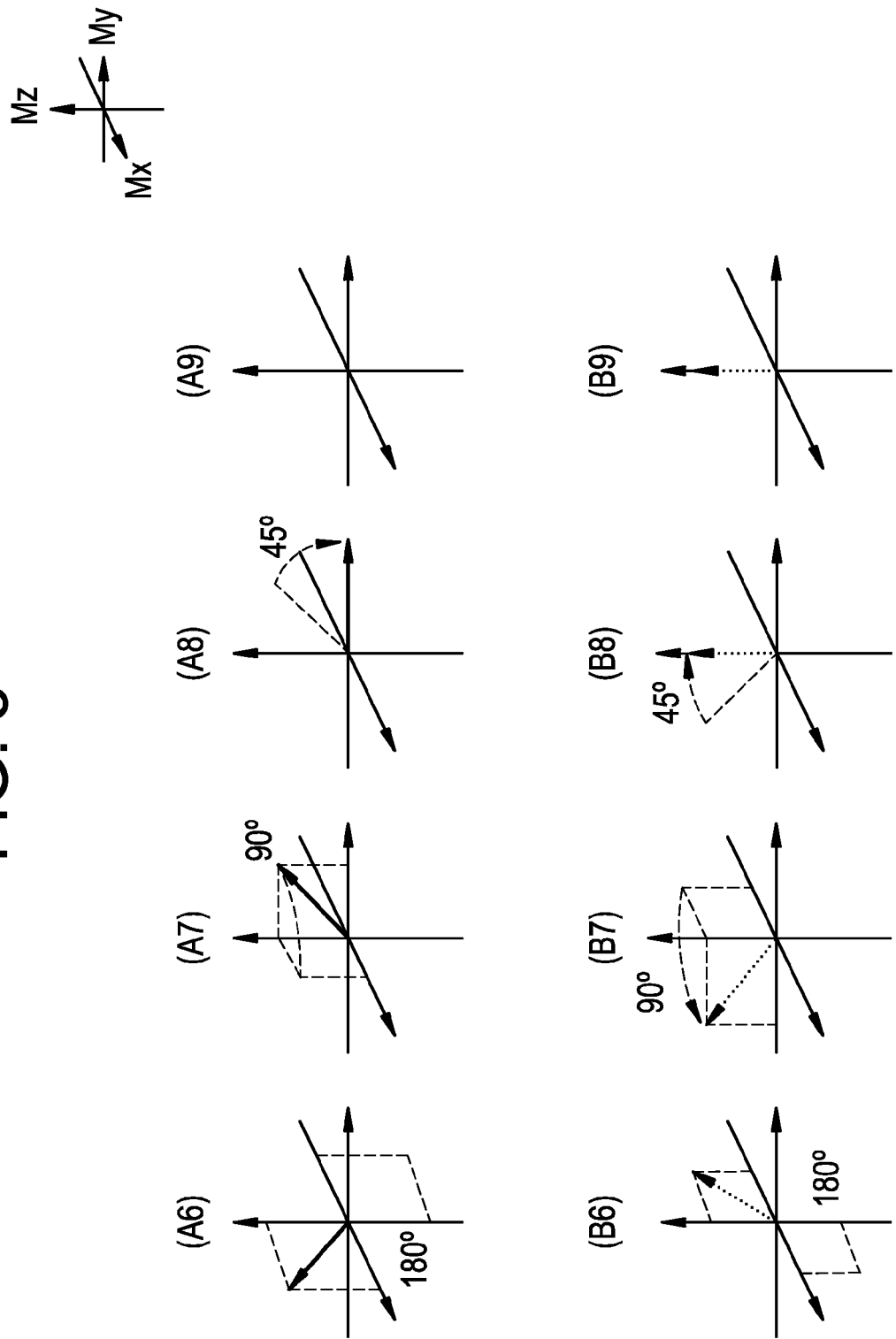

In FIG. 7 and FIG. 8, (A1), (A2), (A3), (A4), (A5) (A6), (A7), (A8) and (A9) refer to the behavior of the subject SU regarding the spin S1 at the first velocity V1 sequentially in a time series. Here is shown the behavior regarding the spin S1 where the first velocity V1 is zero, namely in a static state. On the other hand in FIG. 7 and FIG. 8, (B1), (B2), (B3), (B4), (B5), (B6), (B7), (B8) and (B9) refer to the behavior of the subject SU regarding the spin S2 moving at the second velocity V2, faster than the first velocity V1, sequentially in a time series.

Further in FIG. 7, (A1) and (B1) show the state manifested by the spins S1 and S2 at a first time point t21 in the pulse sequence chart shown in FIG. 6. In FIG. 7, (A2) and (B2) show the state manifested by the spins S1 and S2 at a second time point t22 in the pulse sequence chart shown in FIG. 6. In FIG. 7, (A3) and (B3) show the state manifested by the spins S1 and S2 at a third time point t23 in the pulse sequence chart shown in FIG. 6. In FIG. 7, (A4) and (B4) show the state manifested by the spins S1 and S2 at a fourth time point t24 in the pulse sequence chart shown in FIG. 6. In FIG. 7, (A5) and (B5) show the state manifested by the spins S1 and S2 at a fifth time point t25 in the pulse sequence chart shown in FIG. 6. In FIG. 8, (A6) and (B6) show the state manifested by the spins S1 and S2 at a sixth time point t26 in the pulse sequence chart shown in FIG. 6. In FIG. 8, (A7) and (B7) show the state manifested by the spins S1 and S2 at a seventh time point t27 in the pulse sequence chart shown in FIG. 6. In FIG. 8, (A8) and (B8) show the state manifested by the spins S1 and S2 at an eighth time point t28 in the pulse sequence chart shown in FIG. 6. In FIG. 8, (A9) and (B9) show the state manifested by the spins S1 and S2 at a ninth time point t29 in the pulse sequence chart shown in FIG. 6.

As shown in FIG. 6, when executing the pulse sequence PS, the scanning unit 2 successively transmits, as in Mode for Implementation 1, to the subject SU the first RF pulse RF1, the velocity encoding gradient pulse Gv, the second RF pulse RF2 and the killer pulse Gk as preparation pulses. Here as shown in FIG. 6, as in Mode for Implementation 1, the first RF pulse RF1, the velocity encoding gradient pulse Gv and the second RF pulse RF2 are so transmitted successively to the subject SU as to equalize the first time interval τ1 between the central time point tr1 of the time during which the first RF pulse RF1 is transmitted and the central time point tv of the time during which the velocity encoding gradient pulse Gv is transmitted and the second time interval τ2 between the central time point tv of the time during which the velocity encoding gradient pulse Gv is transmitted and the central time point tr2 of the time during which the second RF pulse RF2 is transmitted. And after that, as in Mode for Implementation 1, the killer pulse Gk is further transmitted. In this mode for implementation, as in Mode for Implementation 1, the scanning unit 2 so transmits these first RF pulse RF1 and second RF pulse RF2 as to make the flip angle 45°.

And apart from these, in this mode for implementation, as shown in FIG. 6, a third RF pulse RF3 which flips the spin at a different flip angle from the spin flipping by the first RF pulse RF1 and the second RF pulse RF2 is transmitted. Here, the scanning unit 2 so performs the transmission to the subject SU that the central time point tr3 of the time during which this third RF pulse RF3 is transmitted matches the central time point τc1 of the first time interval τ1 within the first time interval τ1 between the central time point tr1 of the time during which the first RF pulse RF1 is transmitted and the central time point tv of the time during which the velocity encoding gradient pulse Gv is transmitted.

In this mode for implementation, the scanning unit 2 so transmits the third RF pulse RF3 that spins are flipped at a flip angle of 180° along the xz plane containing the magnetostatic direction z and the x direction orthogonal to the magnetostatic direction z and the y direction.

And as further shown in FIG. 6, a fourth RF pulse RF4 which flips spins at the same flip angle as the flip angle at which the third RF pulse RF3 flips spins is transmitted. Here, the scanning unit 2 so performs the transmission to the subject SU that the central time point tr4 of the time during which this fourth RF pulse RF4 is transmitted matches the central time point τc2 of the second time interval τ2 within the second time interval τ2 between the central time point tv of the time during which the velocity encoding gradient pulse Gv is transmitted and the central time point tr2 of the time during which the second RF pulse RF2 is transmitted.

In this mode for implementation, the scanning unit 2 so transmits the fourth RF pulse RF4 as to flip spins at a flip angle of 180° along the xz plane as in transmitting the third RF pulse RF3.

In this way, the third RF pulse RF3 and the fourth RF pulse RF4 are so transmitted that the central time point tr3 of the time during which the third RF pulse RF3 is transmitted and the central time point tr4 of the time during which the fourth RF pulse RF4 is transmitted are symmetric forward and backward in the time axis direction with the central time point tv of the time during which the velocity encoding gradient pulse Gv is transmitted as the axis.

The various preparation pulses will be described in due order.

First, as shown in FIG. 6, the first RF pulse RF1 is transmitted to the subject SU.

Here, as shown in FIG. 6, the scanning unit 2 transmits the first RF pulse RF1, which is a rectangular pulse, from the first time point t21 until the second time point t22 as in Mode for Implementation 1. In this mode for implementation, as indicated by FIG. 7 (A1) and FIG. 7 (B1), the scanning unit 2 transmits the first RF pulse RF1 to the spins S1 and S2 of protons whose magnetization vector is oriented in the magnetostatic direction z in the subject SU. And as indicated by FIG. 7 (A2) and FIG. 7 (B2), the magnetization vector of the spins S1 and S2 is flipped to be along the yz plane.

More specifically, as indicated by FIG. 7 (A1) and FIG. 7 (B1), the first RF pulse RF1 of which the flip angle is 45° and the phase is in the x direction is transmitted to the spins S1 and S2 of which the longitudinal magnetization is M0 and the transverse magnetization is zero and, as indicated by FIG. 7 (A2) and FIG. 7 (B2), the vector of magnetization by the spins S1 and S2 is inclined from the 0° direction to the 45° direction on the yz plane.

Next, as shown in FIG. 6, the third RF pulse RF3 is transmitted to the subject SU.

Here, as shown in FIG. 6, the scanning unit 2 so transmits the third RF pulse RF3, which is a rectangular pulse, to achieve a flip angle of 180° and a phase in the y direction from the third time point t23 until the fourth time point t24.

More specifically, as indicated by FIG. 7 (A3) and FIG. 7(B3), the scanning unit 2 transmits the third RF pulse RF3 to the spins S1 and S2 which are inverted by unevenness of the magnetostatic field by 90° from the yz plane and whose magnetization vector on the xz plane is inclined in the 45° direction for instance and, as indicated by FIG. 7 (A4) and FIG. 7 (B4), the spins S1 and S2 are flipped by a flip angle of 180° so as to incline their magnetization vector by 225° on the xz plane.

Next, as shown in FIG. 6, the velocity encoding gradient pulse Gv is transmitted to the subject SU.

Here, as shown in FIG. 6, the scanning unit 2 transmits the velocity encoding gradient pulse Gv from the fourth time point t24 until the fifth time point t25 in the same way as in Mode for Implementation 1. And as indicated by FIG. 7 (A5) and FIG. 7 (B5), the phase of the spin S1 of the first velocity V1 and the phase of the spin S2 of the second velocity V2, which is faster than that first velocity V1, are mutually shifted.

More specifically, as indicated by FIG. 7 (A5) and FIG. 7 (B5), the velocity encoding gradient pulse Gv is transmitted so as to mutually shift the phase of the spin S1 of protons whose first velocity V1 is zero and which is in a static state and the phase of the spin S2 of protons in a moving state of moving at the second velocity V2, which is faster than that first velocity V1, by 180°. Thus, the spin S1 of protons in the static state, as indicated by FIG. 7 (A5), the transmission of the velocity encoding gradient pulse Gv causes the magnetization vector of the spin S1 to be turned by unevenness of the magnetostatic field by 180° causes it to vary from the 225° direction on the yz plane to the 135° direction. On the other hand regarding the spin S2 of protons in the moving state, as indicated by FIG. 7 (B5), while it is turned by 180° by the transmission of the velocity encoding gradient pulse Gv, unevenness of the magnetostatic field turns it by another 180° to a total of 360°, resulting in a return to the original position.

Next, as shown in FIG. 6, the fourth RF pulse RF4 is transmitted to the subject SU.

Here, as shown in FIG. 6, the scanning unit 2 so transmits the fourth RF pulse RF4, which is a rectangular pulse, to achieve a flip angle of 180° and a phase in the y direction from the fifth time point t25 until the sixth time point t26.

More specifically, as indicated by FIG. 8 (A6) and FIG. 8 (B6), the scanning unit 2 transmits the fourth RF pulse RF4 to flip the magnetization vector of the spins S1 and S2 by a flip angle of 180° on the xz plane.

Next, as shown in FIG. 6, the second RF pulse RF2 is transmitted to the subject SU.

Here, as shown in FIG. 6, the scanning unit 2 transmits the second RF pulse RF2, which is a rectangular pulse, from the seventh time point t27 until the eighth time point t28.

More specifically, as indicated by FIG. 8 (A7) and FIG. 8 (B7), the scanning unit 2 transmits the second RF pulse RF2 to the spins S1 and S2 whose magnetization vector is inverted by unevenness of the magnetostatic field by 90° and, as indicated by FIG. 8 (A8) and FIG. 8 (B8), causes the magnetization vector of the spins S1 and S2 to be flipped by a flip angle of 45°.

Next, as shown in FIG. 6, the killer pulse Gk is transmitted to the subject SU.

Here, as shown in FIG. 6, the scanning unit 2 transmits the killer pulse Gk from the eighth time point t28 till the ninth time point t29. And as indicated by FIG. 8 (A9) and FIG. 8 (B9), the transverse magnetization of the spins S1 and S2 flipped by the second RF pulse RF2 is extinguished.

In other words, by transmitting the killer pulse Gk as indicated by FIG. 8 (A9), the magnetization vector of the spin S1 in a static state oriented in the 90° direction on the yz plane is dispersed in phase and thereby extinguished.

As described above, when the preparation sequence PS is executed in this mode for implementation, in addition to the preparation pulses in the first mode for implementation, the third RF pulse RF3 and the fourth RF pulse for flipping spins by a flip angle of 180° are transmitted. Here, the scanning unit 2 so transmits the third RF pulse to the subject SU that the central time point tr3 of the time during which this third RF pulse RF3 is transmitted matches the central time point τc1 of the first time interval τ1 within the first time interval τ1 between the central time point tr1 of the time during which the first RF pulse RF1 is transmitted and the central time point tv of the time during which the velocity encoding gradient pulse Gv is transmitted.

Also, the scanning unit 2 so transmits the fourth RF pulse RF4 to the subject SU that the central time point tr4 of the time during which this fourth RF pulse RF4 is transmitted matches the central time point τc2 of the second time interval τ2 within the second time interval τ2 between the central time point tv of the time during which the velocity encoding gradient pulse Gv is transmitted and the central time point tr2 of the time during which the second RF pulse RF2 is transmitted.

For this reason, as shown in FIG. 7 and FIG. 8 referred to above, the spin S1 in a static state phase-shifted by unevenness of the magnetostatic field during the execution of the preparation sequence PS returns in the y direction at the seventh time point t27 (cf. FIG. 8 (A8)) after the third RF pulse RF3 and the fourth RF pulse which flip spins by a flip angle of 180° are transmitted, and the influence of the unevenness of the magnetostatic field is thereby cancelled.

Therefore in this mode for implementation, as in Mode for Implementation 1, an image in which the part moving at a prescribed moving velocity is emphasized in the subject SU can be obtained, and at the same time the quality of images can be improved because the influence of the unevenness of the magnetostatic field can be cancelled. [0117]

Mode for Implementation 3

Mode for Implementation 3 pertaining to the present invention will be described below.

Figure 9:
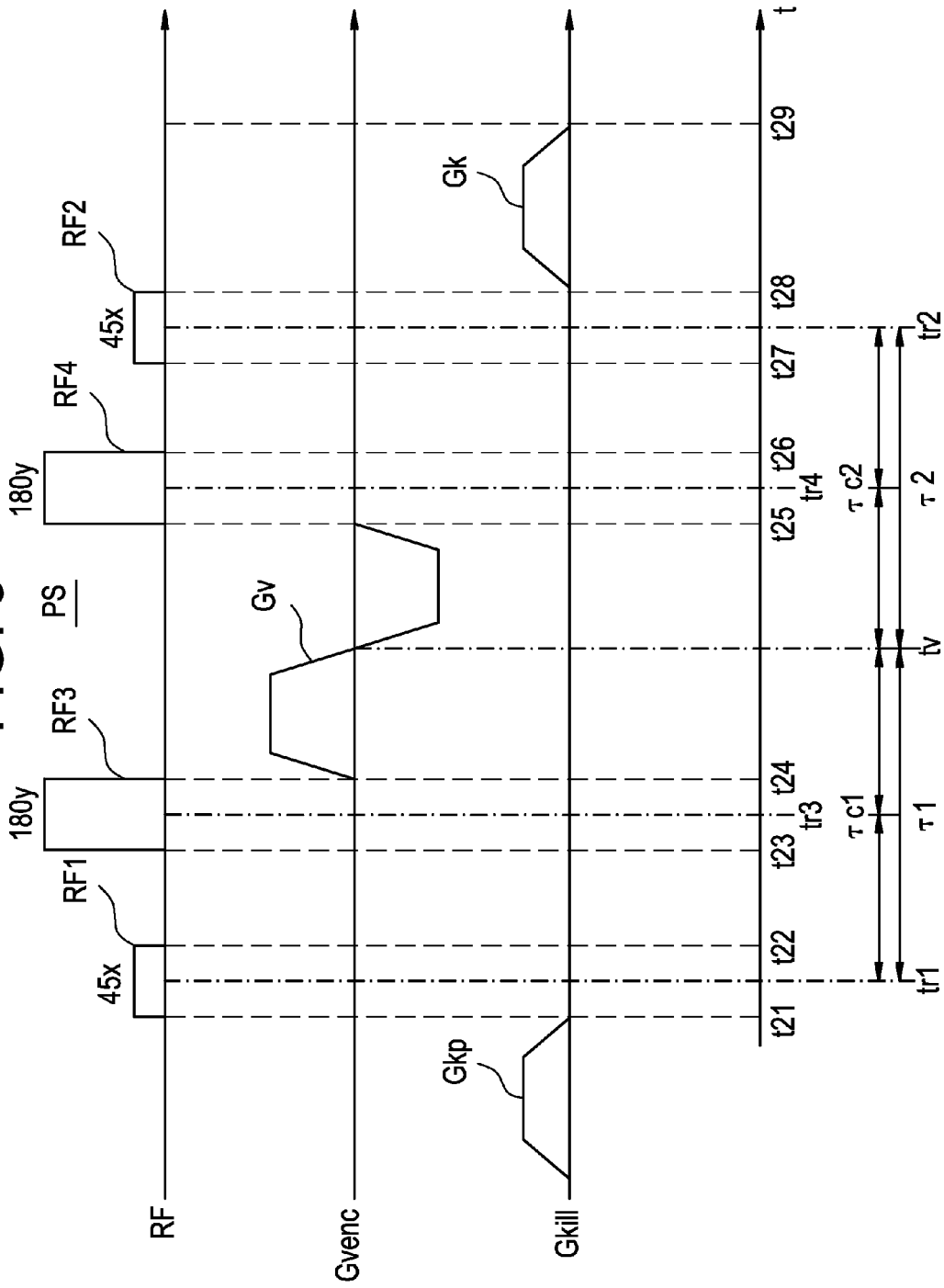
FIG. 9 is a pulse sequence chart showing the preparation sequence PS Mode for Implementation 3 pertaining to the invention.

FIG. 9 is a pulse sequence chart showing the preparation sequence PS Mode for Implementation 3 pertaining to the invention.

In FIG. 9, RF denotes the time axis of transmitting RF pulses; Gvenc, the time axis of transmitting velocity encoding pulses; and Gkill, the time axis of transmitting killer pulses, for each of which the horizontal axis represents the time t and the vertical axis, the pulse intensity. Here, Gvenc and Gkill are the time axes of transmitting gradient pulses, each being a time axis in at least one of the slice selecting direction, the phase encoding direction and the frequency encoding direction.

The preparation sequence PS executed in imaging the subject SU in this mode for implementation differs from that in Mode for Implementation 2 (FIG. 6). This mode for implementation is similar to Mode for Implementation 2 except in this respect. For this reason, description of duplicated parts will be dispensed with.

In this mode for implementation, as shown in FIG. 9, the scanning unit 2 transmits as a preparation pulse, in addition to the preparation pulses in Mode for Implementation 2, a killer pulse Gkp for generating a gradient magnetic field to extinguishing the transverse magnetization of spins in the subject SU before transmitting the first RF pulse RF1.

Since the transverse magnetization of spins is extinguished before transmitting the first RF pulse RF1, this mode for implementation can serve to further improve the quality of images in addition to the effects of Mode for Implementation 2.

Mode for Implementation 4

Mode for Implementation 4 pertaining to the present invention will be described below.

Figure 10:
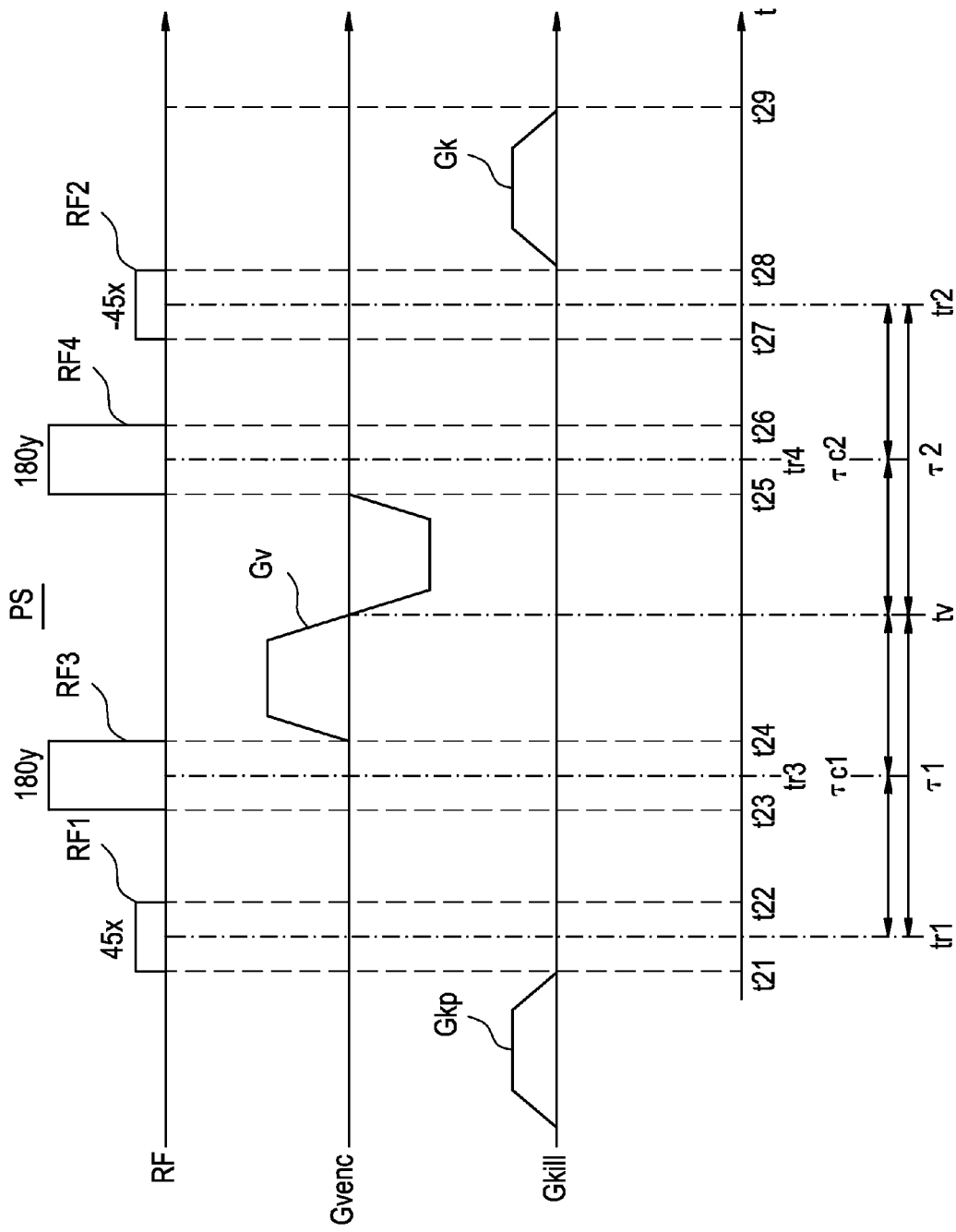
FIG. 10 is a pulse sequence chart showing the preparation sequence PS Mode for Implementation 4 pertaining to the invention.

FIG. 10 is a pulse sequence chart showing the preparation sequence PS in Mode for Implementation 4 pertaining to the invention.

In FIG. 10, RF denotes the time axis of transmitting RF pulses; Gvenc, the time axis of transmitting velocity encoding pulses; and Gkill, the time axis of transmitting killer pulses, for each of which the horizontal axis represents the time t and the vertical axis, the pulse intensity. Here, Gvenc and Gkill are the time axes of transmitting gradient pulses, each being a time axis in at least one of the slice selecting direction, the phase encoding direction and the frequency encoding direction.

The preparation sequence PS executed in imaging the subject SU in this mode for implementation differs from that in Mode for Implementation 3 (FIG. 9). This mode for implementation is similar to Mode for Implementation 3 except in this respect. For this reason, description of duplicated parts will be dispensed with.

In this mode for implementation, as shown in FIG. 10, the scanning unit 2 so transmits the second RF pulse RF2 among the preparation pulses in Mode for Implementation 3 as to flip spins by a flip angle of −45°.

For this reason, in this mode for implementation, a high signal intensity can be obtained for spins in a static state while a low signal intensity can be obtained for spins in a moving state, and therefore images of high contrast between the parts in a static state and the parts in a moving state can be obtained.

Mode for Implementation 5

Mode for Implementation 5 pertaining to the present invention will be described below.

Figure 11:
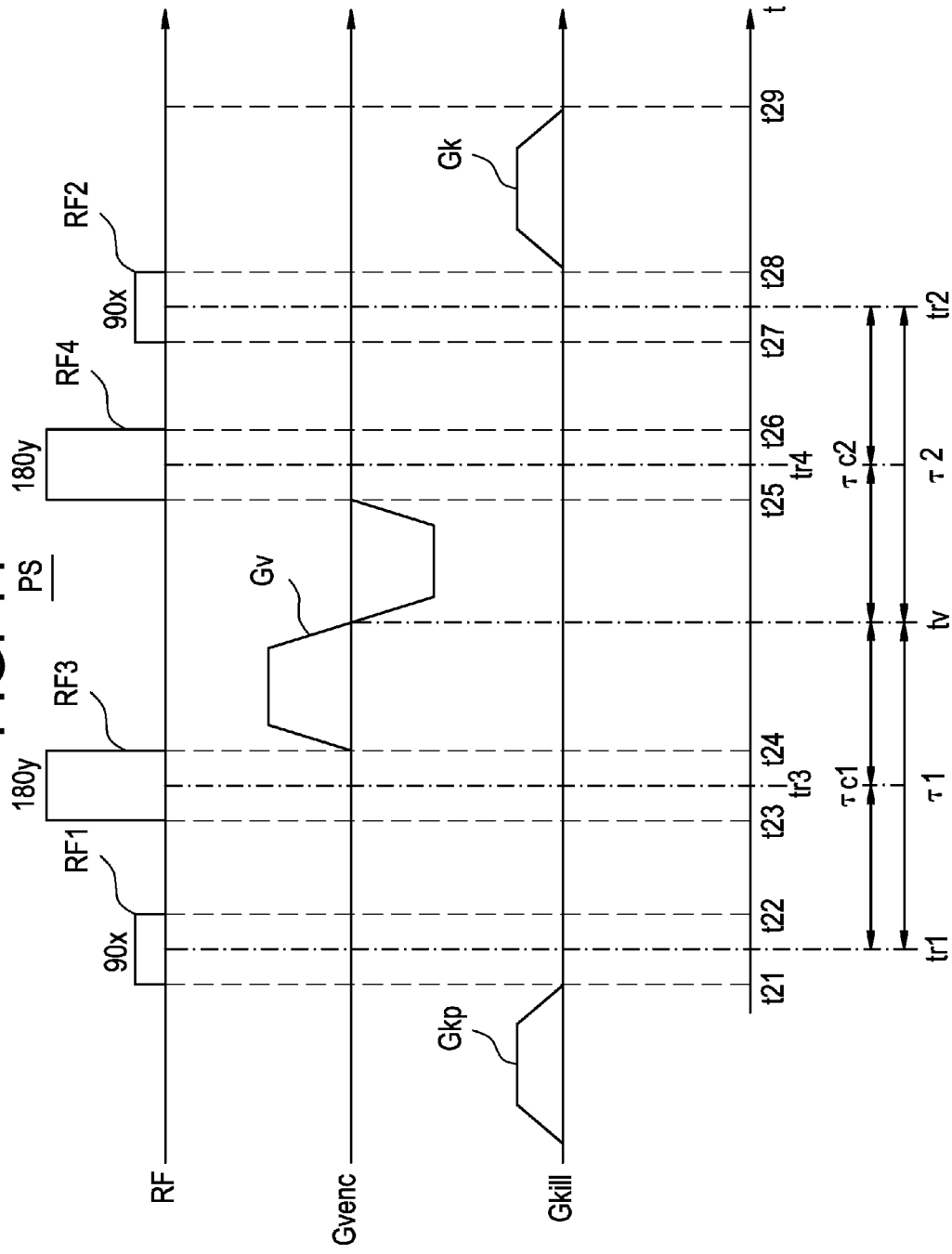
FIG. 11 is a pulse sequence chart showing the preparation sequence PS Mode for Implementation 5 pertaining to the invention.

FIG. 11 is a pulse sequence chart showing the preparation sequence PS in Mode for Implementation 5 pertaining to the invention.

In FIG. 11, RF denotes the time axis of transmitting RF pulses; Gvenc, the time axis of transmitting velocity encoding pulses; and Gkill, the time axis of transmitting killer pulses, for each of which the horizontal axis represents the time t and the vertical axis, the pulse intensity. Here, Gvenc and Gkill are the time axes of transmitting gradient pulses, each being a time axis in at least one of the slice selecting direction, the phase encoding direction and the frequency encoding direction.

The preparation sequence PS executed in imaging the subject SU in this mode for implementation differs from that in Mode for Implementation 3 (FIG. 9). This mode for implementation is similar to Mode for Implementation 3 except in this respect. For this reason, description of duplicated parts will be dispensed with.

In this mode for implementation, as shown in FIG. 11, the scanning unit 2 so transmits the first RF pulse RF1 and the second RF pulse RF2 among the preparation pulses in Mode for Implementation 3 as to flip spins by a flip angle of 90°.

For this reason, in this mode for implementation, it is possible to invert the longitudinal magnetization spins in a static state to the negative while the longitudinal magnetization spins in a moving state can inverted to the positive, and accordingly images of high contrast between the parts in a static state and the parts in a moving state can be obtained as in Mode for Implementation 3.

Mode for Implementation 6

Mode for Implementation 6 pertaining to the present invention will be described below.

Figure 12:
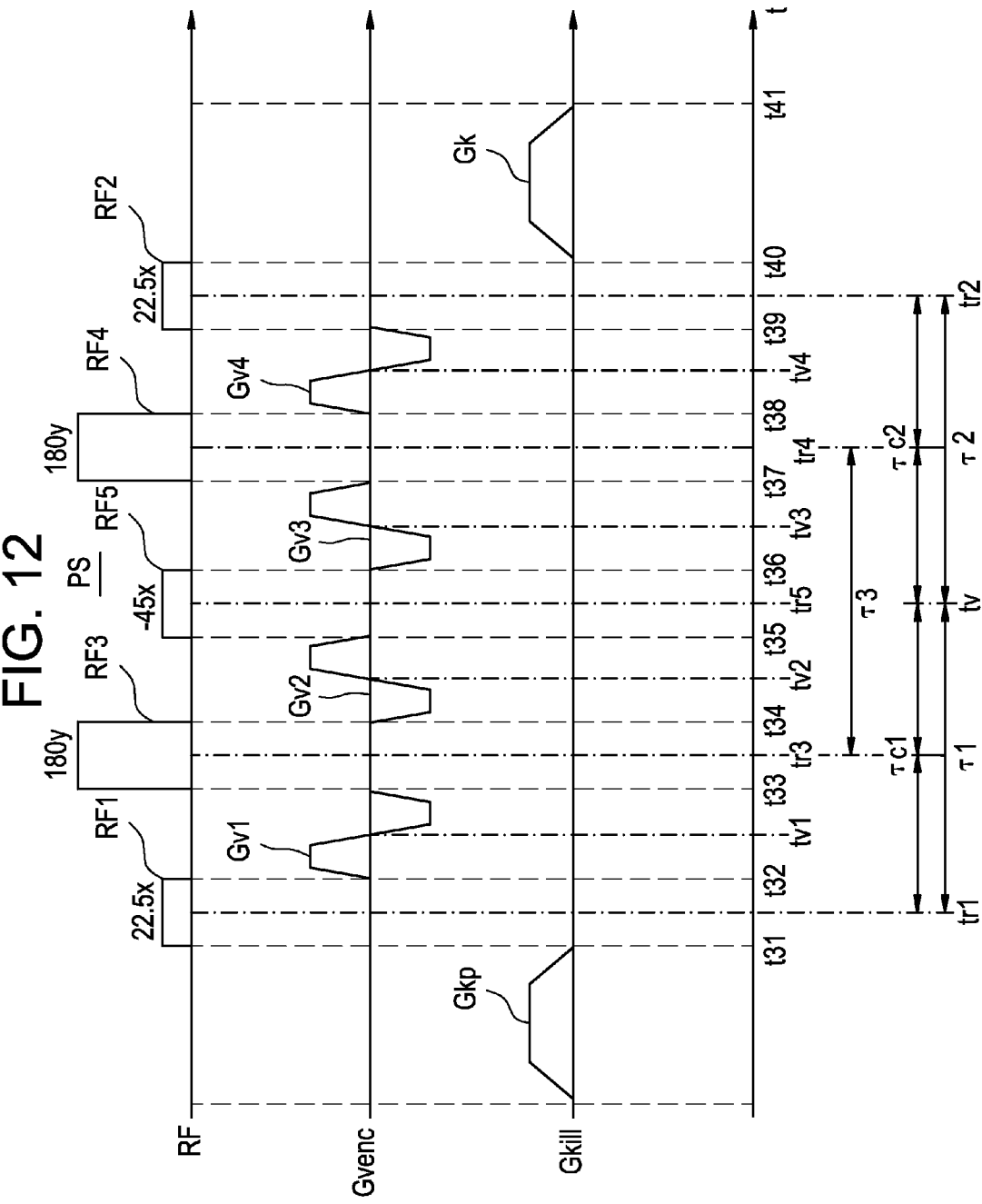
FIG. 12 is a pulse sequence chart showing the preparation sequence PS Mode for Implementation 6 pertaining to the invention.

FIG. 12 is a pulse sequence chart showing the preparation sequence PS in Mode for Implementation 6 pertaining to the invention.

In FIG. 12, RF denotes the time axis of transmitting RF pulses; Gvenc, the time axis of transmitting velocity encoding pulses; and Gkill, the time axis of transmitting killer pulses, for each of which the horizontal axis represents the time t and the vertical axis, the pulse intensity. Here, Gvenc and Gkill are the time axes of transmitting gradient pulses, each being a time axis in at least one of the slice selecting direction, the phase encoding direction and the frequency encoding direction.

The preparation sequence PS executed in imaging the subject SU in this mode for implementation differs from that in Mode for Implementation 3 (FIG. 9). This mode for implementation is similar to Mode for Implementation 3 except in this respect. For this reason, description of duplicated parts will be dispensed with.

In this mode for implementation, as shown in FIG. 12, the scanning unit 2 so transmits the first RF pulse RF1 and the second RF pulse RF2 to achieve a flip angle of 22.5 (and a phase in the x direction. In other words, the scanning unit 2 so transmits the first RF pulse RF1 and the second RF pulse RF2 to the subject SU as to flip spins by a flip angle of 22.5(.

As shown in FIG. 12, the scanning unit 2 transmits successively a first velocity encoding gradient pulse Gv1 and a second velocity encoding gradient pulse Gv2, which is inverse in polarity to that first velocity encoding gradient pulse Gv1 on the time axis, as the velocity encoding gradient pulses Gv, such that, within the first time interval (1, the central time point tv1 of the time during which the first velocity encoding gradient pulse Gv1 is transmitted and the central time point tv2 of the time during which the second velocity encoding gradient pulse Gv2 is transmitted symmetrically hold between them on the time axis of the central time point (c1 of the first time interval (1. Along with this, the scanning unit 2 transmits successively a third velocity encoding gradient pulse Gv3 and a fourth velocity encoding gradient pulse Gv4, which is inverse in polarity to that third velocity encoding gradient pulse Gv3, such that, within the second time interval τ2, the central time point tv3 of the time during which the third velocity encoding gradient pulse Gv3 is transmitted and the central time point tv4 of the time during which the fourth velocity encoding gradient pulse Gv4 is transmitted symmetrically hold between them on the time axis of the central time point τc2 of the second time interval τ2.

In other words, the scanning unit 2 so performs transmission that the central time points tv1, tv2, tv3 and tv4 of the times during which the first velocity encoding gradient pulse Gv1, the second velocity encoding gradient pulse Gv2, the third velocity encoding gradient pulse Gv3 and the fourth velocity encoding gradient pulse Gv4 are symmetrically aligned on the time axis with respect to the central time points tv of the times during which the first velocity encoding gradient pulse Gv1, the second velocity encoding gradient pulse Gv2, the third velocity encoding gradient pulse Gv3 and the third encoding gradient pulse Gv4 are transmitted.

Besides that, as shown in FIG. 12, the scanning unit 2 transmits as another preparation pulse a fifth RF pulse RF5 of which the flip angle is −45° and the phase is in the x direction. In other words, the scanning unit 2 so transmits the fifth RF pulse RF5 as to flip spins along the yz plane by a flip angle of −45°. Here, the scanning unit 2 transmits to the subject SU the fifth RF pulse RF5 such that, after the transmission of the second velocity encoding gradient pulse Gv2, before the transmission of the third velocity encoding gradient pulse Gv3 and within a third time interval τ3 between the central time point tr3 of the time during which the third RF pulse RF3 is transmitted and the central time point tr4 of the time during which the fourth RF pulse RF4 is transmitted, the central time point tr5 of the time during which the fifth RF pulse RF5 is transmitted matches the central time point τc3 of the third time interval τ3. Thus, another RF pulse is so transmitted as to match the central time point of the time during which the two RF pulses whose flip angle is 180° are transmitted.

As described above, in this mode for implementation, the quality of images can be improved by so transmitting each of the first velocity encoding gradient pulse Gv1, the second velocity encoding gradient pulse Gv2, the third velocity encoding gradient pulse Gv3 and the fourth velocity encoding gradient pulse Gv4 as to hold between each of the third RF pulse and the fourth RF pulse whose flip angle is 180°. Further, as shown in FIG. 6, while a large area velocity encoding gradient pulses are needed in the previously described mode for implementation, since the area (time-integrated value) of each velocity encoding gradient pulse can be reduced by transmitting velocity encoding gradient pulses before and after the transmission of 180° RF pulses, the duration of preparation sequence execution can be shortened in this mode for implementation.

Further in this mode for implementation, the quality of images can be improved by so transmitting the fifth RF pulse RF5 as to be held between the third RF pulse and the fourth RF pulse whose flip angle is 180°. And this enables different velocity encoding gradient pulses to be transmitted in multiple directions at the same time, and the signal intensity formula to be altered to a different form from Mathematical Expression (1).

Mode for Implementation 7

Mode for Implementation 7 pertaining to the present invention will be described below.

Figure 13:
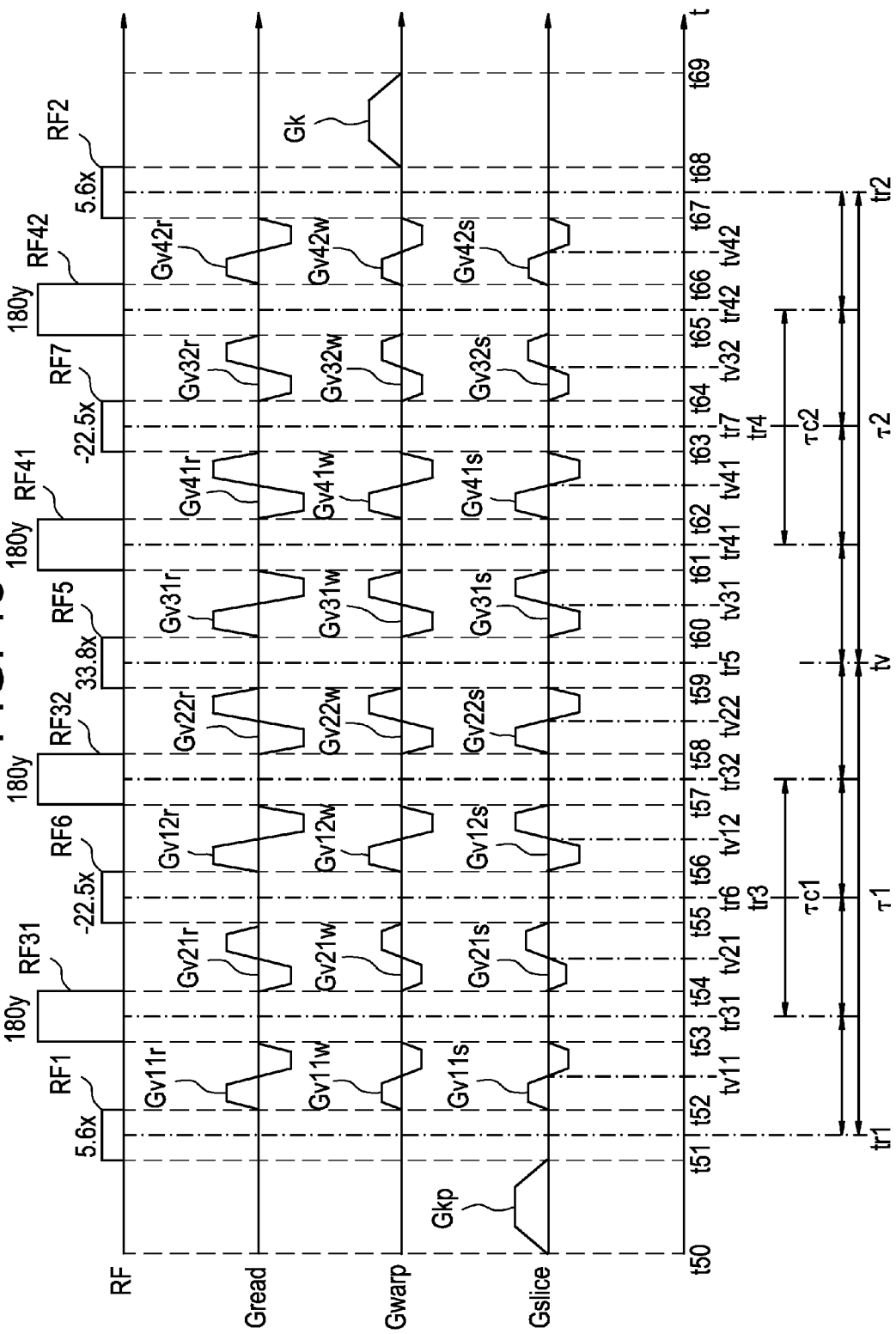
FIG. 13 is a pulse sequence chart showing the preparation sequence PS Mode for Implementation 7 pertaining to the invention.

FIG. 13 is a pulse sequence chart showing the preparation sequence PS in Mode for Implementation 7 pertaining to the invention.

In FIG. 13, RF denotes the time axis of transmitting RF pulses; Gread, the time axis on which gradient pulses are transmitted in the frequency encoding direction in the subject SU; Gwarp, the time axis on which gradient pulses are transmitted in the phase encoding direction; and Gslice, the time axis on which gradient pulses are transmitted in the slice selection encoding direction, for each of which the horizontal axis represents the time t and the vertical axis, the pulse intensity.

The preparation sequence PS executed in imaging the subject SU in this mode for implementation differs from that in Mode for Implementation 6 (FIG. 12). This mode for implementation is similar to Mode for Implementation 6 except in this respect. For this reason, description of duplicated parts will be dispensed with.

In this mode for implementation, as shown in FIG. 13, the scanning unit 2 so transmits the first RF pulse RF1 and the second RF pulse RF2 as to have a flip angle of 5.6° and a phase in the x direction. And as shown in FIG. 13, the scanning unit 2 so transmits the fifth RF pulse RF5 as to have a flip angle of 33.8° and a phase in the x direction. In other words, the scanning unit 2 so transmits the first RF pulse RF1 and the second RF pulse RF2 that spins are flipped along the yz plane at a flip angle of 5.6°, and at the same time the scanning unit 2 so transmits the fifth RF pulse RF5 to the subject SU that spins are flipped along the yz plane at a flip angle of 33.8°.

Also in this mode for implementation, as shown in FIG. 13, the scanning unit 2 transmits successively to the subject SU as the third RF pulses RF3 two RF pulses RF31 and RF32 which flip spins by a flip angle of 180°, so as to be within the first time interval τ1 and be symmetric with respect to the time axis with the central time point τc1 of the time interval τ1 in-between. Further, the scanning unit 2 transmits successively to the subject SU as the fourth RF pulses RF4 two RF pulses RF41 and RF42 which flip spins by a flip angle of 180°, so as to be within the second time interval τ2 and be symmetric with respect to the time axis with the central time point τc2 of the second time interval τ2 in-between.

And as shown in FIG. 13, the scanning unit 2 transmits successively, as velocity encoding gradient pulses Gv, first velocity encoding gradient pulses Gv11r, Gv11w, Gv11s, Gv12r, Gv12w and Gv12s and second velocity encoding gradient pulses Gv21r, Gv21w, Gv21s, Gv22r, Gv22w and Gv22s, which are inverse in polarity to those first velocity encoding gradient pulses Gv11r, Gv11w, Gv11s, Gv12r, Gv12w and Gv12s with respect to the time axis, so as to be symmetric with respect to the time axis with the central time points tr31 and tr32 of the times during which two RF pulses RF31 and RF32 are transmitted as third RF pulses RF3 in-between. And the scanning unit 2 transmits successively third velocity encoding gradient pulses Gv31r, Gv31w, Gv31s, Gv32r, Gv32w, Gv32s and fourth velocity encoding gradient pulses Gv41r, Gv41w, Gv41s, Gv42r, Gv42w and Gv42s, which are inverse in polarity to those third velocity encoding gradient pulses Gv31r, Gv31w, Gv31s, Gv32r, Gv32w and Gv32s, so as to be symmetric with respect to the time axis with the central time points tr41 and tr42 of the times during which two RF pulses RF41 and RF42 are transmitted as four RF pulses RF4 in-between. Here, the scanning unit 2 transmits the velocity encoding gradient pulses to the slice selecting direction Gslice, the phase encoding direction Gwarp and the frequency encoding direction Gread so as to reduce correlations on the respective axes.

Besides these, the scanning unit 2 transmits as preparation pulses a sixth RF pulse RF6 and a seventh RF pulse RF7 of which the flip angle is −22.5° and the phase is in the x direction. Here, out of a plurality of RF pulses RF31 and RF32 successively transmitted as third RF pulses RF3, the scanning unit 2 so transmits the sixth RF pulse RF6 to the subject SU that the central time point tr6 of the time during which the sixth RF pulse RF6 is transmitted comes between a pair of RF pulses RF31 and RF32 and matches the central time point tr3 of the time during which the pair of RF pulses RF31 and RF32 are transmitted. And along with this, the scanning unit 2 transmits to the subject SU a seventh RF pulse RF7 out of a plurality of RF pulses RF41 and RF42 successively transmitted as fourth RF pulse RF4, so that the central time point tr7 of the time during which the seventh RF pulse RF7 is transmitted comes between a pair of RF pulses RF41 and RF42 and matches the central time point tr4 of the time during which the pair of RF pulses RF41 and RF42 are transmitted. In this mode for implementation, the sixth RF pulse R6 is so transmitted to the subject SU that the central time point tr6 of the time during which the sixth RF pulse R6 is transmitted matches the central time point tr3 of the time during which the plurality of RF pulses RF31 and RF32 are transmitted as third RF pulses RF3 to flip spins along the yz plane by a flip angle of −22.5°. And similarly, in order that the central time point tr7 of the time during which the seventh RF pulse RF7 is transmitted matches the central time point tr4 of the time during which the plurality of RF pulses RF41 and RF42 are transmitted as fourth RF pulses RF4, this seventh RF pulse RF7 is transmitted to the subject SU to flip spins along the yz plane by a flip angle of −22.5°.

For this reason, in this mode for implementation, since each of the velocity encoding gradient pulses is transmitted in the slice selecting direction, the phase encoding direction and the frequency encoding direction, in obtaining three-dimensional area images of the subject SU, images with high contrast between the parts in a static state and the parts in a moving state can be obtained similarly to Mode for Implementation 6.

Mode for Implementation 8

Mode for Implementation 8 pertaining to the present invention will be described below.

Figure 14:
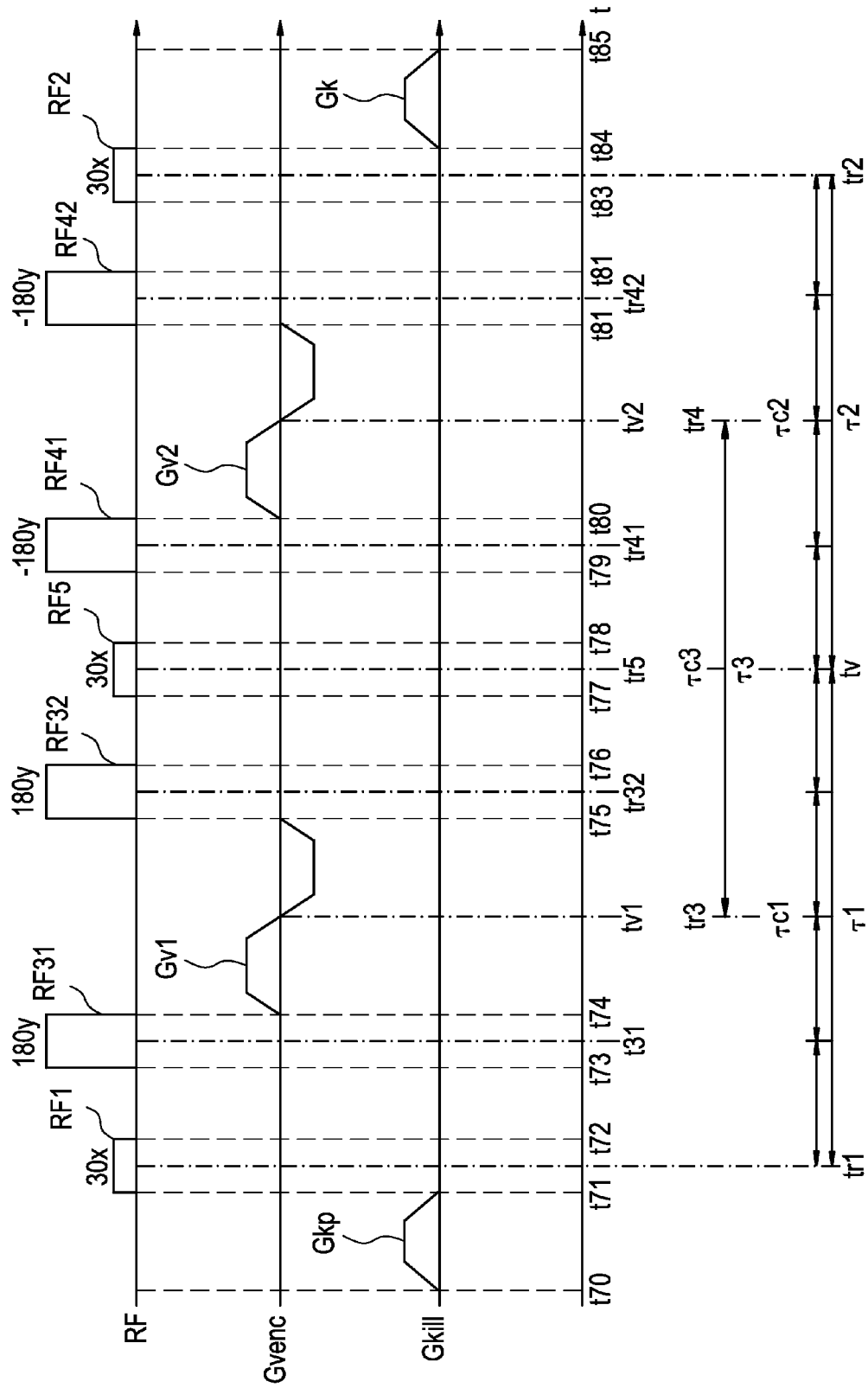
FIG. 14 is a pulse sequence chart showing the preparation sequence PS Mode for Implementation 8 pertaining to the invention.

FIG. 14 is a pulse sequence chart showing the preparation sequence PS in Mode for Implementation 8 pertaining to the invention.

In FIG. 14, RF denotes the time axis of transmitting RF pulses; Gvenc, the time axis of transmitting velocity encoding pulses; and Gkill, the time axis of transmitting killer pulses, for each of which the horizontal axis represents the time t and the vertical axis, the pulse intensity. Here, Gvenc and Gkill are the time axes of transmitting gradient pulses, each being a time axis in at least one of the slice selecting direction, the phase encoding direction and the frequency encoding direction.

The preparation sequence PS executed in imaging the subject SU in this mode for implementation differs from that in Mode for Implementation 3 (FIG. 9). This mode for implementation is a preparation sequence based on the so-called MLEV (Malcolm Levitt) method, and is similar to Mode for Implementation 3 except in this respect. For this reason, description of duplicated parts will be dispensed with.

In this mode for implementation, as shown in FIG. 14, the scanning unit 2 so transmits the first RF pulse RF1 and the second RF pulse RF2 as to have a flip angle of 30° and a phase in the x direction. In other words, the scanning unit 2 so transmits the first RF pulse RF1 and the second RF pulse RF2 to the subject SU that spins are flipped along the yz plane at a flip angle of 30°.

Further in this mode for implementation, as shown in FIG. 14, the scanning unit 2 transmits successively to the subject SU as the third RF pulses RF3 two RF pulses RF31 and RF32 of which the flip angle is 180° and the phase in the y direction so as to be symmetric on the time axis within the first time interval τ1 with the central time point τc1 of the first time interval τ1 in-between. And it transmits successively to the subject SU as the fourth RF pulses RF4 two RF pulses RF41 and RF42 of which the flip angle is −180° and the phase in the y direction so as to be symmetric on the time axis within the second time interval τ2 with the central time point τc2 of the second time interval τ2 in-between.

And as shown in FIG. 14, the scanning unit 2 so transmits the first velocity encoding gradient pulse Gv1 as the velocity encoding gradient pulse Gv to be held between the two RF pulses RF31 and RF32 transmitted as the third RF pulses RF3 on the time axis, and so transmits the second velocity encoding gradient pulse Gv2 as the velocity encoding gradient pulse Gv to be held between the two RF pulses RF41 and RF42 transmitted as the fourth RF pulses RF4 on the time axis. Here, the scanning unit 2 so performs transmission that the central time points tv1 and tv2 of the times during which the first velocity encoding gradient pulse Gv1 and the second velocity encoding gradient pulse Gv2 are transmitted are symmetrically aligned on the time axis with respect to the central time point tv of the time during which the first velocity encoding gradient pulse Gv1 and the second velocity encoding gradient pulse Gv2 are transmitted.

Besides that, as shown in FIG. 14, the scanning unit 2 transmits as a preparation pulse the fifth RF pulse of which the flip angle is 30° and the phase is in the x direction. In other words, the scanning unit 2 so transmits the fifth RF pulse RF5 as to flip spins along the yz plane by a flip angle of 30°. Here, the scanning unit 2 transmits to the subject SU the fifth RF pulse RF5 so that, after the transmission of the first velocity encoding gradient pulse Gv1, before the transmission of the second velocity encoding gradient pulse Gv2, and within the third time interval τ3 between the central time point tr3 of the time during which two RF pulses RF31 and RF32 are transmitted as the third RF pulses RF3 and the central time point tr4 of the time during which two RF pulses RF41 and RF42 are transmitted as the fourth RF pulses RF4, the central time point tr5 of the time during which the fifth RF pulse RF5 is transmitted matches the central time point τc3 of the third time interval τ3.

Therefore in this mode for implementation, as in Mode for Implementation 3, the quality of images can be improved because the influence of the unevenness of the magnetostatic field can be cancelled by inverted pulses whose flip angles are 180° and −180°.

Mode for Implementation 9

Mode for Implementation 9 pertaining to the present invention will be described below.

Figure 15:
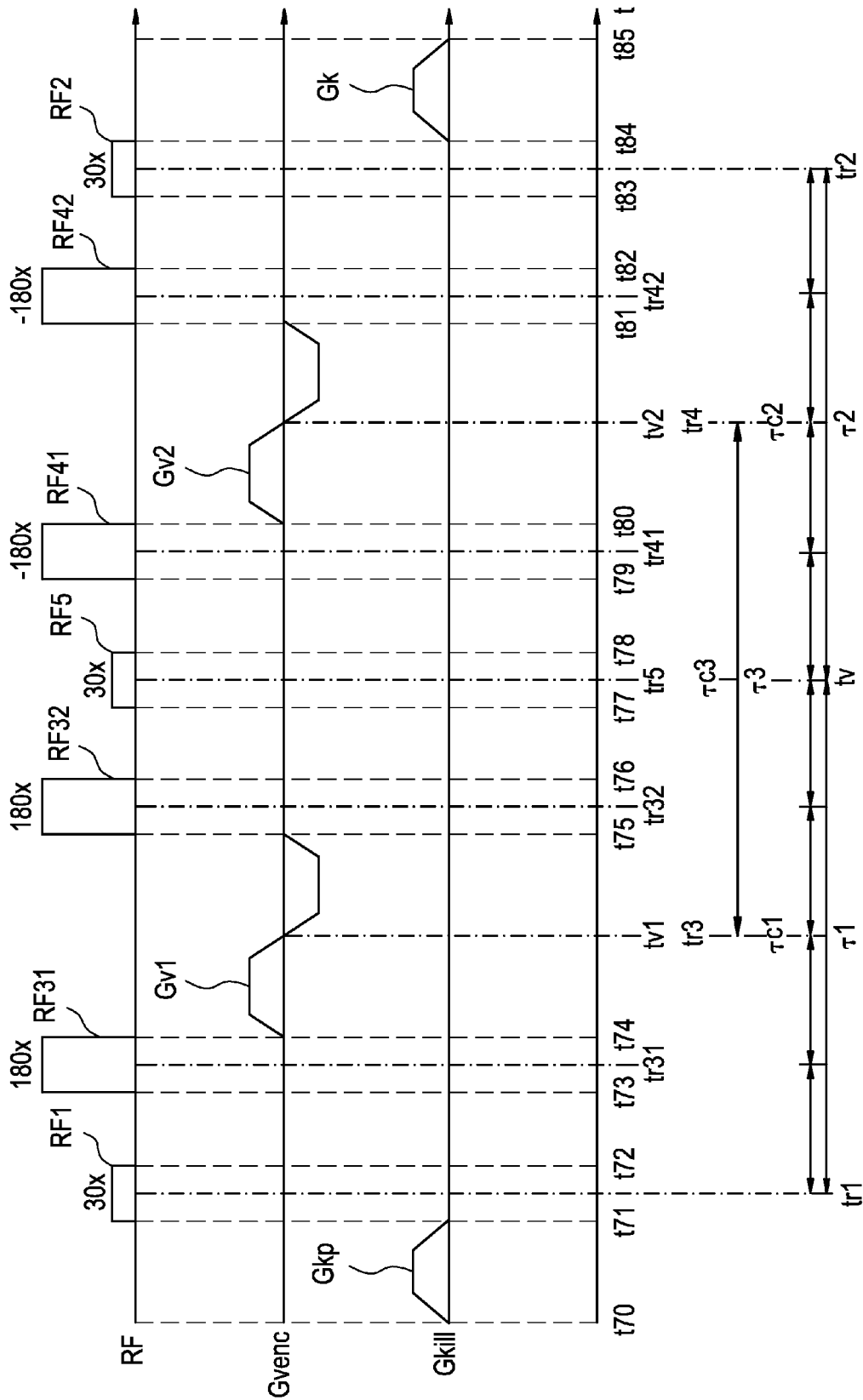
FIG. 15 is a pulse sequence chart showing the preparation sequence PS Mode for Implementation 9 pertaining to the invention.

FIG. 15 is a pulse sequence chart showing the preparation sequence PS in Mode for Implementation 9 pertaining to the invention.

In FIG. 15, RF denotes the time axis of transmitting RF pulses; Gvenc, the time axis of transmitting velocity encoding pulses; and Gkill, the time axis of transmitting killer pulses, for each of which the horizontal axis represents the time t and the vertical axis, the pulse intensity. Here, Gvenc and Gkill are the time axes of transmitting gradient pulses, each being a time axis in at least one of the slice selecting direction, the phase encoding direction and the frequency encoding direction.

The preparation sequence PS executed in imaging the subject SU in this mode for implementation differs from that in Mode for Implementation 8 (FIG. 14). This mode for implementation is a preparation sequence based on the so-called CP (Carr-Purcell) method, and is similar to Mode for Implementation 8 except in this respect. For this reason, description of duplicated parts will be dispensed with.

In this mode for implementation, as shown in FIG. 15, the scanning unit 2 as in Mode for Implementation 8 transmits successively to the subject SU as the third RF pulses RF3 two RF pulses RF31 and RF32 of which the flip angle is 180° and the phase is in the x direction ao as to be symmetric on the time axis within the first time interval τ1 with the central time point τc1 of the first time interval τ1 in-between. On the other hand, it transmits successively to the subject SU as the fourth RF pulses RF4 two RF pulses RF41 and RF42 of which the flip angle is 180° and the phase is in the x direction so as to be symmetric on the time axis within the second time interval τ2 with the central time point τc2 of the second time interval τ2 in-between.

Therefore in this mode for implementation, as in Mode for Implementation 8, the quality of images can be improved because the influence of the unevenness of the magnetostatic field can be cancelled by an inverted pulse whose flip angle is 180°.

Mode for Implementation 10

Mode for Implementation 10 pertaining to the present invention will be described below.

Figure 16:
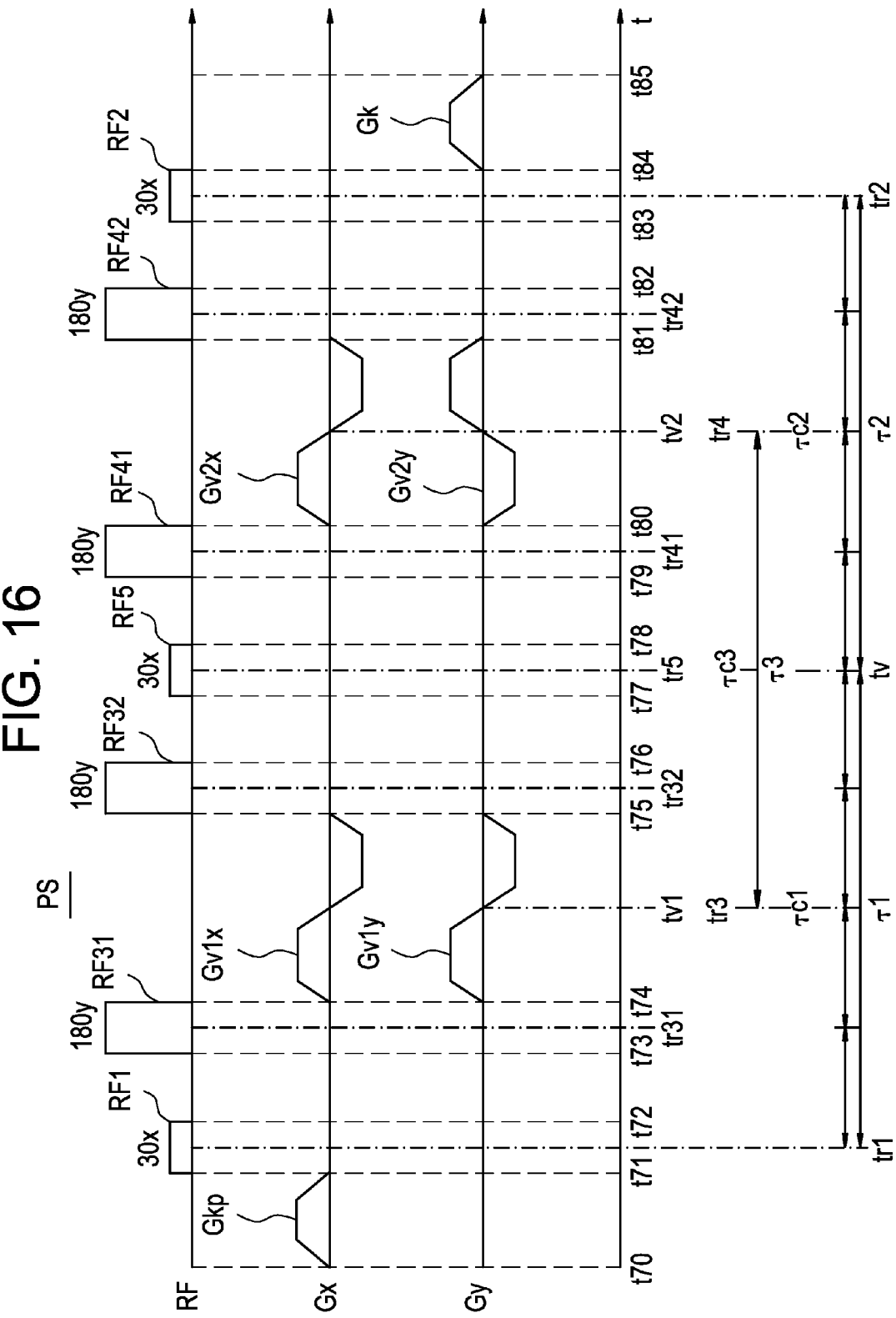
FIG. 16 is a pulse sequence chart showing the preparation sequence PS Mode for Implementation 10 pertaining to the invention.

FIG. 16 is a pulse sequence chart showing the preparation sequence PS in Mode for Implementation 10 pertaining to the invention.

In FIG. 16, RF denotes the time axis of transmitting RF pulses; Gx, the time axis of gradient pulses to be transmitted in the subject SU in the x direction; and Gy, the time axis of gradient pulses to be transmitted in the subject SU in the y direction, for each of which the horizontal axis represents the time t and the vertical axis, the pulse intensity.

The preparation sequence PS executed in imaging the subject SU in this mode for implementation differs from that in Mode for Implementation 8 (FIG. 14). This mode for implementation is similar to Mode for Implementation 8 except in this respect. For this reason, description of duplicated parts will be dispensed with.

In this mode for implementation, as shown in FIG. 16, the scanning unit 2 as in Mode for Implementation 8 transmits successively to the subject SU as the third RF pulses RF3, two RF pulses RF31 and RF32 of which the flip angle is 180° and the phase is in the y direction so as to be symmetric on the time axis within the first time interval τ1 with the central time point τc1 of the first time interval τ1 in-between.

On the other hand, the scanning unit 2 transmits successively to the subject SU as the fourth RF pulses RF4, two RF pulses RF41 and RF42 of which the flip angle is 180° and the phase is in the y direction, so as to be symmetric on the time axis within the second time interval τ2 with the central time point τc2 of the second time interval τ2 in-between.

And as shown in FIG. 16, the scanning unit 2 so transmits first velocity encoding gradient pulses Gv1x and Gv1y respectively in the x direction and the y direction as velocity encoding gradient pulses Gv so as to be held between the two RF pulses RF31 and RF32 whose flip angle is 180° and which are transmitted as the third RF pulses RF3 on the time axis. And along with these, the scanning unit 2 transmits second velocity encoding gradient pulses Gv2x and Gv2y respectively in the x direction and the y direction as velocity encoding gradient pulses Gv so as to be held between the two RF pulses RF41 and RF42 whose flip angle is 180° and which are transmitted as the fourth RF pulses RF4 on the time axis.

In this mode for implementation, since the velocity encoding gradient pulses are respectively transmitted in the x direction and the y direction, images with high contrast between the parts in a static state and the parts in a moving state can be obtained similarly to Mode for Implementation 8.

Mode for Implementation 11

Mode for Implementation 11 pertaining to the present invention will be described below.

Figure 17:
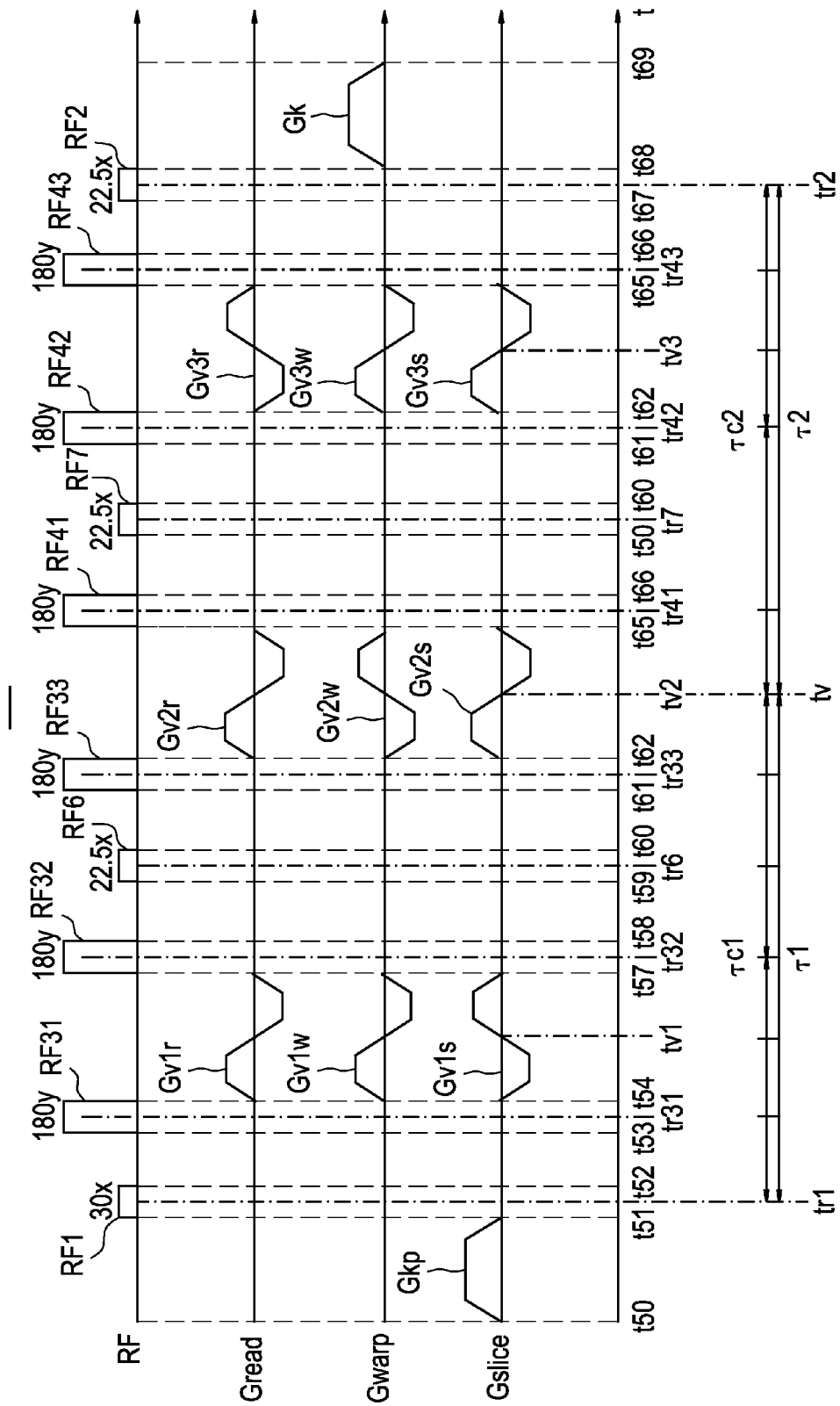
FIG. 17 is a pulse sequence chart showing the preparation sequence PS Mode for Implementation 11 pertaining to the invention.

FIG. 17 is a pulse sequence chart showing the preparation sequence PS in Mode for Implementation 11 pertaining to the invention.

In FIG. 17, RF denotes the time axis of transmitting RF pulses; Gread, the time axis on which gradient pulses are transmitted in the frequency encoding direction in the subject SU; Gwarp, the time axis on which gradient pulses are transmitted in the phase encoding direction; and Gslice, the time axis on which gradient pulses are transmitted in the slice selection encoding direction, for each of which the horizontal axis represents the time t and the vertical axis, the pulse intensity.

The preparation sequence PS executed in imaging the subject SU in this mode for implementation differs from that in Mode for Implementation 3 (FIG. 9). This mode for implementation is similar to Mode for Implementation 3 except in this respect. For this reason, description of duplicated parts will be dispensed with.

In this mode for implementation, as shown in FIG. 17, the scanning unit 2 so transmits the first RF pulse RF1 and the second RF pulse RF2 as to have a flip angle of 22.5° and a phase in the x direction. In other words, the scanning unit 2 transmits the first RF pulse RF1 and the second RF pulse RF2 to the subject SU such that spins are flipped along the yz plane at a flip angle of 22.5°.

Further in this mode for implementation, as shown in FIG. 17, the scanning unit 2 transmits successively to the subject SU three RF pulses RF31, RF32 and RF33 of which the flip angle is 180° and the phase is in the y direction as the third RF pulses RF3, so as to be symmetric on the time axis, within the first time interval τ1 with the central time point τc1 of the first time interval τ1 in-between.

Further as the fourth RF pulses RF4, it so transmits successively to the subject SU three RF pulses RF41, RF42 and RF43 of which the flip angle is 180° and the phase is in the y direction as to be symmetric on the time axis within the second time interval τ2 with the central time point τc2 of the second time interval τ2 in-between.

As shown in FIG. 17, the scanning unit 2 transmits successively to the subject SU, as velocity encoding gradient pulses Gv, first velocity encoding gradient pulses Gv1r, Gv1w and Gv1s, second velocity encoding gradient pulses Gv2r, Gv2w and Gv2s, and third velocity encoding gradient pulses Gv3r, Gv3w and Gv3s.

Here, the scanning unit 2 so performs transmission that the central time points tv1, tv2 and tv3 of the times during which the first velocity encoding gradient pulse Gv1r, Gv1w and Gv1s, the second velocity encoding gradient pulse Gv2r, Gv2w and Gv2s, and the third velocity encoding gradient pulse Gv3r, Gv3w and Gv3s are transmitted are symmetrically aligned on the time axis with respect to the central time point tv of the time during which the first velocity encoding gradient pulses Gv1r, Gv1w and Gv1s, the second velocity encoding gradient pulses Gv2r, Gv2w and Gv2s and the third velocity encoding gradient pulses Gv3r, Gv3w and Gv3s are transmitted.

More specifically, it transmits the first velocity encoding gradient pulses Gv1r, Gv1w and Gv1s in the frequency encoding direction Gread, the phase encoding direction Gwarp and the slice selection encoding direction Gslice, respectively, so as to be held on the time axis between the former two RF pulses RF31 and RF32 out of the three RF pulses RF31, RF32 and RF33 transmitted as the third RF pulses RF3. Also, it transmits the second velocity encoding gradient pulses Gv2r, Gv2w and Gv2s in the frequency encoding direction Gread, the phase encoding direction Gwarp and the slice selection encoding direction Gslice, respectively, so as to be held on the time axis between the third RF pulses RF3 consisting of three RF pulses RF31, RF32 and RF33 and the fourth RF pulse RF4 consisting of three RF pulses RF41, RF42 and RF43. And it transmits the third velocity encoding gradient pulses Gv3r, Gv3w and Gv3s in the frequency encoding direction Gread, the phase encoding direction Gwarp and the slice selection encoding direction Gslice, respectively, so as to be held on the time axis between the latter two RF pulses RF42 and RF43 out of the three RF pulses RF41, RF42 and RF43 transmitted as the fourth RF pulses RF4. Here, the scanning unit 2 transmits the respective velocity encoding gradient pulses in the frequency encoding direction Gread, the phase encoding direction Gwarp and the slice selection encoding direction Gslice so as to reduce correlations on the respective axes.

Besides that, the scanning unit 2 transmits as preparation pulses a sixth RF pulse RF6 and a seventh RF pulse RF7 of which the flip angle is 22.5° and the phase is in the x direction.

Here, the scanning unit 2 so performs transmission that the central time points tr6 and tr7 of the times during which the sixth RF pulse RF6 and the seventh RF pulse RF7 are respectively transmitted are symmetrically aligned on the time axis with respect to the central time point tv of the time during which the first velocity encoding gradient pulses Gv1r, Gv1w and Gv1s, the second velocity encoding gradient pulses Gv2r, Gv2w and Gv2s and the third velocity encoding gradient pulses Gv3r, Gv3w and Gv3s are transmitted.

More specifically, the scanning unit 2 transmits the sixth RF pulse RF6 so as to be held on the time axis between the latter two RF pulses RF32 and RF33 out of the three RF pulses RF31, RF32 and RF33 transmitted as the third RF pulses RF3.

Also, it so transmits the seventh RF pulse RF7 as to be held on the time axis between the former two RF pulses RF41 and RF42 out of the three RF pulses RF41, RF42 and RF43 transmitted as the fourth RF pulses RF4.

For this reason, in this mode for implementation, since each of the velocity encoding gradient pulses is transmitted in the slice selecting direction, the phase encoding direction and the frequency encoding direction, in the three-dimensional area of the subject SU, images with high contrast between the parts in a static state and the parts in a moving state can be obtained similarly to Mode for Implementation 6.

Mode for Implementation 12

Mode for Implementation 12 pertaining to the present invention will be described below.

Figure 18:
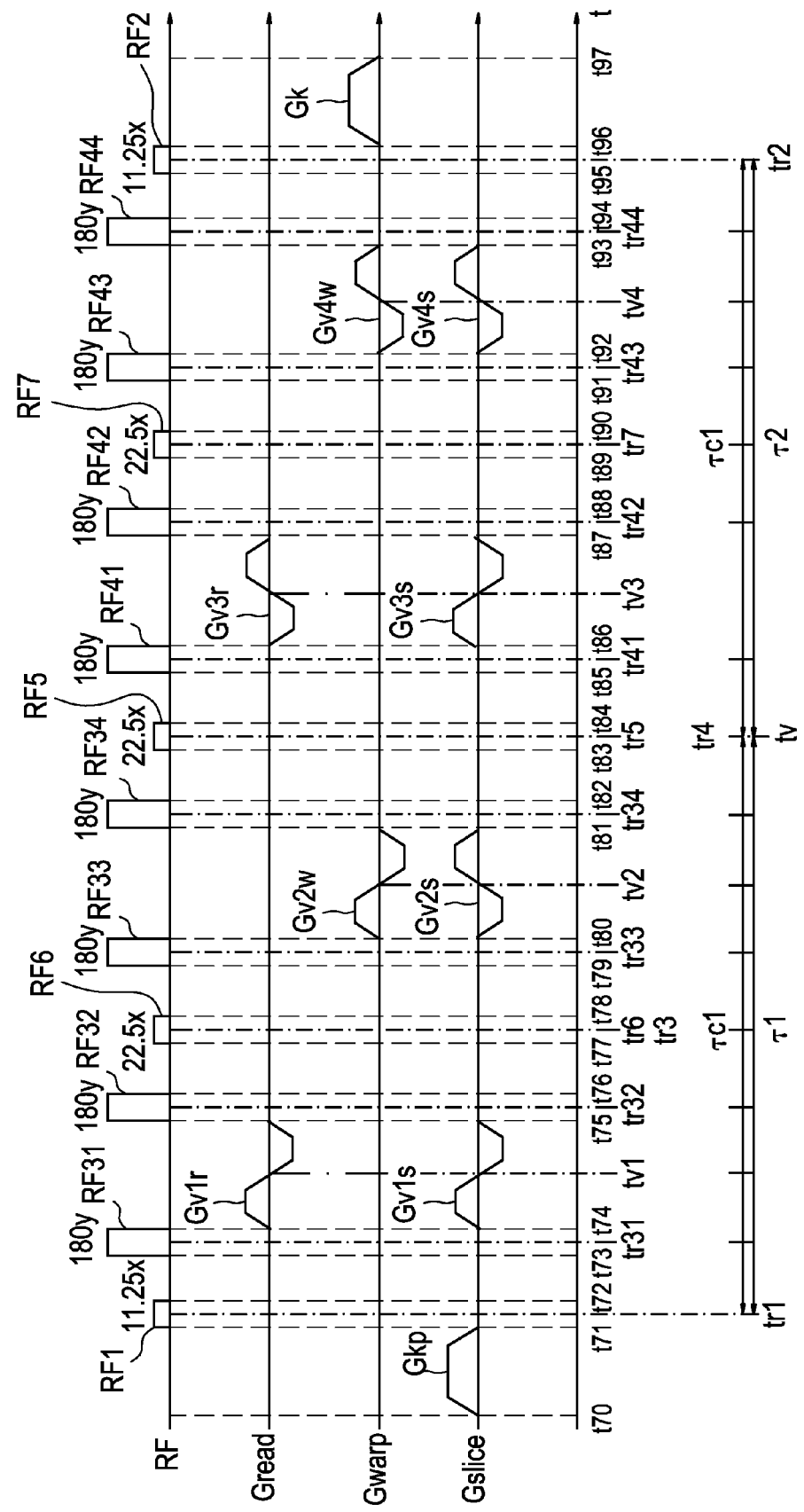
FIG. 18 is a pulse sequence chart showing the preparation sequence PS Mode for Implementation 12 pertaining to the invention.

FIG. 18 is a pulse sequence chart showing the preparation sequence PS in Mode for Implementation 12 pertaining to the invention.

In FIG. 18, RF denotes the time axis of transmitting RF pulses; Gread, the time axis on which gradient pulses are transmitted in the frequency encoding direction in the subject SU; Gwarp, the time axis on which gradient pulses are transmitted in the phase encoding direction; and Gslice, the time axis on which gradient pulses are transmitted in the slice selection encoding direction, for each of which the horizontal axis represents the time t and the vertical axis, the pulse intensity.

The preparation sequence PS executed in imaging the subject SU in this mode for implementation differs from that in Mode for Implementation 3 (FIG. 9). This mode for implementation is similar to Mode for Implementation 3 except in this respect. For this reason, description of duplicated parts will be dispensed with.

In this mode for implementation, as shown in FIG. 18, the scanning unit 2 transmits the first RF pulse RF1 and the second RF pulse RF2 so as to have a flip angle of 11.25° and a phase in the x direction. In other words, the scanning unit 2 transmits the first RF pulse RF1 and the second RF pulse RF2 to the subject SU such that spins are flipped along the yz plane at a flip angle of 11.25°.

Further as shown in FIG. 18, the scanning unit 2 transmits successively to the subject SU four RF pulses RF31, RF32, RF33 and RF34 of which the flip angle is 180° and the phase is in the y direction as the third RF pulses RF3, so as to be symmetric on the time axis within the first time interval τ1 with the central time point τc1 of the first time interval τ1 in-between.

Further as the fourth RF pulses RF4, it transmits successively to the subject SU four RF pulses RF41, RF42, RF43 and RF44 of which the flip angle is 180° and the phase is in the y direction so as to be symmetric on the time axis within the second time interval τ2 with the central time point τc2 of the second time interval τ2 in-between.

And as shown in FIG. 18, the scanning unit 2 transmits as velocity encoding gradient pulses Gv first velocity encoding gradient pulses Gv1r and Gv1s, second velocity encoding gradient pulses Gv2w and Gv2, third velocity encoding gradient pulses Gv3r and Gv3s, and fourth velocity encoding gradient pulses Gv4w and Gv4s.

Here, the scanning unit 2 so performs transmission that the central time points tv1, tv2 and tv3 of the times during which the first velocity encoding gradient pulses Gv1r and Gv1s, the second velocity encoding gradient pulses Gv2r and Gv2s, the third velocity encoding gradient pulses Gv3r and Gv3s, and the fourth velocity encoding gradient pulses Gv4w and Gv4s are respectively transmitted are symmetrically aligned on the time axis with respect to the central time point tv of the time during which the first velocity encoding gradient pulses Gv1r and Gv1s, the second velocity encoding gradient pulses Gv2r and Gv2s, the third velocity encoding gradient pulses Gv3r and Gv3s, and the fourth velocity encoding gradient pulses Gv4w and Gv4s are transmitted.

More specifically, the scanning unit 2 transmits the first velocity encoding gradient pulses Gv1r and Gv1s in the frequency encoding direction Gread and the slice selection encoding direction Gslice, respectively, so as to be held on the time axis between the former two RF pulses RF31 and RF32 out of the four RF pulses RF31, RF32, RF33 and RF34 transmitted as the third RF pulses RF3. Also, it transmits the second velocity encoding gradient pulses Gv2w and Gv2s in the phase encoding direction Gwarp and the slice selection encoding direction Gslice, respectively, so as to be held on the time axis between the latter two RF pulses RF33 and RF34 out of the four RF pulses RF31, RF32 and RF33 transmitted as the third RF pulses RF3.

Also, the scanning unit 2 transmits the third velocity encoding gradient pulses Gv3r and Gv3s in the frequency encoding direction Gread and the slice selection encoding direction Gslice, respectively, so as to be held on the time axis between the former two RF pulses RF41 and RF42 out of the four RF pulses RF41, RF42, RF43 and F44 transmitted as the fourth RF pulses RF4. And it transmits the fourth velocity encoding gradient pulses Gv4w and Gv4s in the phase encoding direction Gwarp and the slice selection encoding direction Gslice, respectively, so as to be held on the time axis between the latter two RF pulses RF43 and RF44 out of the four RF pulses RF41, RF42, RF43 and RF44 transmitted as the fourth RF pulses RF4. Here, the scanning unit 2 transmits the respective velocity encoding gradient pulses in the slice selection encoding direction Gslice, the phase encoding direction Gwarp and the frequency encoding direction Gread so as to reduce correlations on the respective axes.

Besides that, as shown in FIG. 18, the scanning unit 2 transmits as preparation pulses a fifth RF pulse RF5, a sixth RF pulse RF6 and a seventh RF pulse RF7 of which the flip angle is 22.5° and the phase is in the x direction.

Here, the scanning unit 2 so performs transmission that the central time points tr5, tr6 and tr7 of the times during which the fifth RF pulse RF5, the sixth RF pulse RF6 and the seventh RF pulse RF7 are respectively transmitted are symmetrically aligned on the time axis with respect to the central time point tv of the time during which the first velocity encoding gradient pulses Gv1r and Gv1s, the second velocity encoding gradient pulses Gv2r and Gv2s, the third velocity encoding gradient pulses Gv3r and Gv3s, and the fourth velocity encoding gradient pulses Gv4w and Gv4s are transmitted.

More specifically, the scanning unit 2 transmits to the subject SU the fifth RF pulse RF5 such that the central time point tr5 of the time during which the fifth RF pulse RF5 is transmitted matches the central time point tv of the time during which the first velocity encoding gradient pulses Gv1r and Gv1s, the second velocity encoding gradient pulses Gv2r and Gv2s, the third velocity encoding gradient pulses Gv3r and Gv3s, and the fourth velocity encoding gradient pulses Gv4w and Gv4s are transmitted.

Further, the scanning unit 2 so transmits the sixth RF pulse RF6 as to be held on the time axis between the central two RF pulses RF32 and RF33 out of the four RF pulses RF31, RF32, RF33 and RF34 transmitted as the third RF pulses RF3.

And the scanning unit 2 so transmits the seventh RF pulse RF7 as to be held on the time axis between the central two RF pulses RF42 and RF43 out of the four RF pulses RF41, RF42, RF43 and RF44 transmitted as the fourth RF pulses RF4.

For this reason, in this mode for implementation, since each of the velocity encoding gradient pulses is transmitted in the slice selecting direction, the phase encoding direction and the frequency encoding direction, in the three-dimensional area of the subject SU, images with high contrast between the parts in a static state and the parts in a moving state can be obtained similarly to Mode for Implementation 6.

Mode for Implementation 13

Mode for Implementation 13 pertaining to the invention will be described below.

Figure 19:
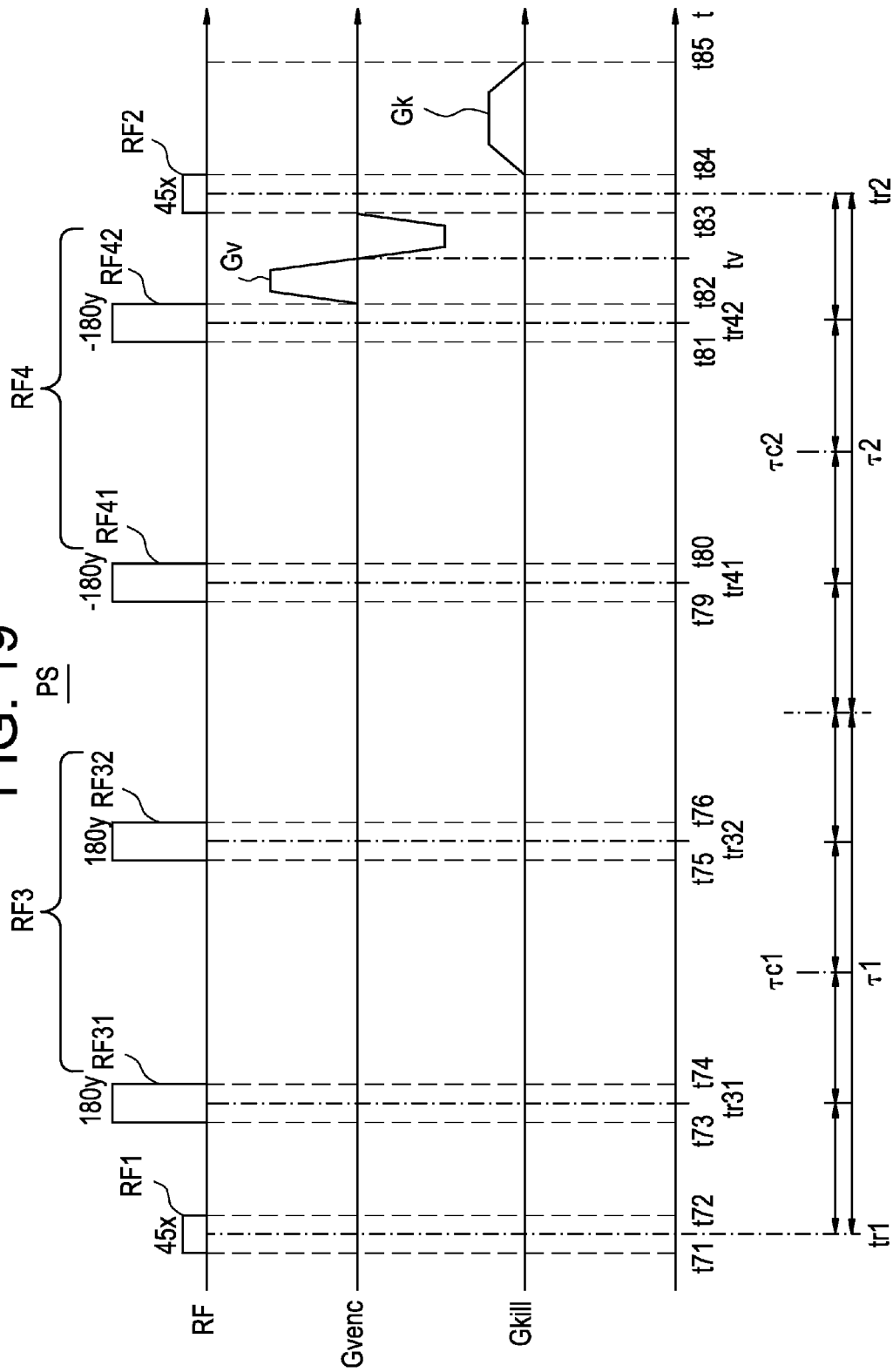
FIG. 19 is a pulse sequence chart showing the preparation sequence PS in Mode for Implementation 13 pertaining to the invention.

FIG. 19 is a pulse sequence chart showing the preparation sequence PS in Mode for Implementation 13 pertaining to the invention.

In FIG. 19, RF denotes the time axis of transmitting RF pulses; Gvenc, the time axis of transmitting velocity encoding gradient pulses; and Gkill, the time axis of transmitting killer pulses, for each of which the horizontal axis represents the time t and the vertical axis, the pulse intensity. Here, Gvenc and Gkill are the time axes of transmitting gradient pulses, each being a time axis in at least one of the slice selecting direction, the phase encoding direction and the frequency encoding direction.

This mode for implementation, as shown in FIG. 19, differs from Mode for Implementation 3 (FIG. 9) in the preparation sequence executed at the time of imaging the subject SU. This mode for implementation, like Mode for Implementation 8, is a preparation sequence based on the MLEV method, and is similar to Mode for Implementation 3 except in this point. For this reason, description of duplicated parts will be omitted.

In this mode for implementation, as shown in FIG. 19, the scanning unit 2 transmits the first RF pulse RF1 and the second RF pulse RF2 to give a flip angle of 45° and a phase in the x direction. Thus, so that spins are flipped by a flip angle of 45° along the yz plane, the scanning unit 2 transmits the first RF pulse RF1 and the second RF pulse RF2 to the subject.

Further in this mode for implementation, as shown in FIG. 19, the scanning unit 2 successively transmits to the subject SU as the third RF pulses RF3 two RF pulses RF31 and RF32 of which the flip angle is 180° and the phase is in the y direction so as to be within the first time interval τ1 and to be symmetrical on the time axis with the central time point τc1 of the first time interval τ1 in-between. And it successively transmits to the subject SU as the fourth RF pulses two RF pulses RF41 and RF42 of which the flip angle is −180° and the phase is in the y direction so as to be within the second time interval τ2 and to be symmetrical on the time axis with the central time point τc2 of the second time interval τ2 in-between.

And, as shown in FIG. 19, the scanning unit 2 successively transmits to the subject the velocity encoding gradient pulses Gv after the transmission of the two RF pulses RF31 and RF32 which are the third RF pulses RF3 and of the two RF pulses RF41 and RF42 which are the fourth RF pulses RF4 and before transmitting the second RF pulses RF2. Here, the scanning unit 2 so transmits the velocity encoding gradient pulses Gv which form a bipolar gradient magnetic field that the central point of the times at which the fourth RF pulses RF4 and the second RF pulses RF2 are transmitted and the central point tv of the times at which the velocity encoding gradient pulses Gv are transmitted match each other.

Since the influence of the magnetostatic non-uniformity (B0 non-uniformity) is cancelled by inverted pulses whose flip angles are 180° and −180° in this mode for implementation as in Mode for Implementation 3, picture quality can be improved. Furthermore in this mode for implementation unlike in Mode for Implementation 8 (cf. FIG. 14), no fifth RF pulses are transmitted between the third RF pulses RF3 and the fourth RF pulses RF4, and the velocity encoding gradient pulses Gv are transmitted only between the fourth RF pulses RF4 and the second RF pulses RF2; it is a technique equivalent to the MLEV method, and can better actualize the effects of the MLEV method than in Mode for Implementation 8 which includes a technique of the CPMG method. Thus, as this mode for implementation permits ready exclusion of the influences of the magnetostatic non-uniformity and the RF magnetic field non-uniformity (B1 non-uniformity) and enables the sturdiness expected of the MLEV method to be manifested, picture quality can be further improved. Actual volunteer tests revealed significant effects, and the blood could be represented more uniformly especially where the FOV was great.

Mode for Implementation 14

Mode for Implementation 14 pertaining to the invention will be described below.

Figure 20:
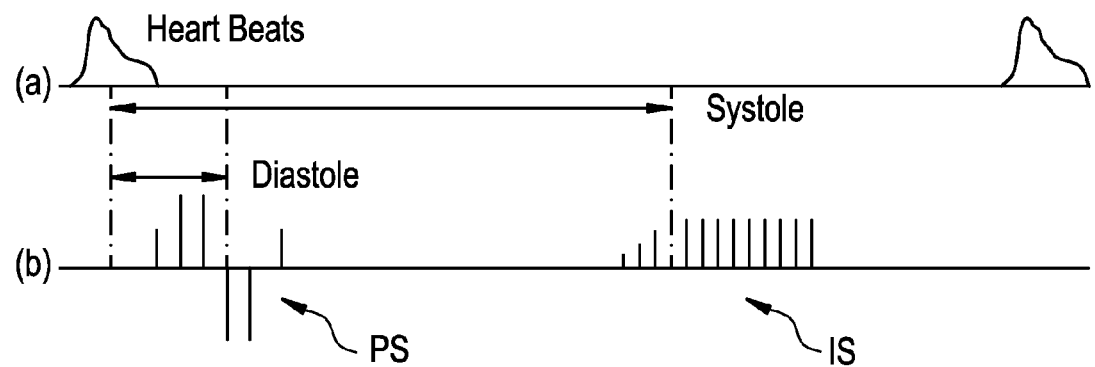
FIG. 20 is a chart showing execution of the preparation sequence PS and imaging sequence IS in Mode for Implementation 14 pertaining to the invention.

FIG. 20 shows how the preparation sequence PS and the imaging sequence IS are executed in Mode for Implementation 14 pertaining to the invention. In FIG. 20, the horizontal axis is the time axis t; (a) shows the trend of the subject's heart beat signals; and (b), the executing timings of the preparation sequence PS and the imaging sequence IS matched with the subject's heart beat signals.

This mode for implementation, as shown in FIG. 20, identifies the executing timings of the preparation sequence PS and the imaging sequence IS. Except in this respect, it is similar to Mode for Implementation 13. For this reason, description of duplicated parts will be omitted.

In this mode for implementation, as shown in FIG. 20, the scanning unit 2, after so executing the preparation sequence PS as to match the systole in heart beating of the subject, so executes the imaging sequence IS as to match the diastole of heart beating.

More specifically, first the velocity of a fluid, such as blood, flowing in the subject is measured by using a phase contrast method synchronized with heart beats, and the timings of the systole and the diastole of the subject's heart beating are identified. After that, the preparation sequence PS and the imaging sequence IS are so executed as to match those identified timings as shown in FIG. 20.

Since in this mode for implementation the preparation sequence PS is executed in the systole, which is a state in which the blood flow is strong in the subject's heart beating, the blood and other static parts can be readily distinguished from each other. Also, as the imaging sequence IS is executed in the diastole, which is a state in which the blood flow is weak in the subject's heart beating, the occurrence of body motion artifacts or the like in the picked-up image is restrained. Further, in the diastole, since the duration of a slower flow is as long as a few hundreds of milliseconds, sufficient imaging data can be acquired. Therefore, this mode for implementation can help further improve picture quality.

Incidentally, the magnetic resonance imaging apparatus 1 in the above-described modes for implementation corresponds to the magnetic resonance imaging apparatus according to the present invention. Also, the scanning unit 2 in the above-described modes for implementation corresponds to the scanning unit according to the invention. Further, the image generating unit 31 in the above-described modes for implementation corresponds to the image generating unit according to the invention. Further, the display unit 33 in the above-described modes for implementation corresponds to the display unit according to the invention.

Also, the implementation of the invention is not limited to the above-described modes for implementation, but various modifications can be adopted.

For instance, when RF pulses are to be transmitted as preparation pulses, they are not limited to the above-stated flip angle values. Further in this case, slice selection may be implemented. Fat restraining methods such as the CHESS (chemical shift selective) method and the spectral IR method may be used in combination. Also, T2 contrast may be regulated by adjusting the time between the first RF pulse and the final RF pulse.

Although the foregoing description of modes for implementation referred to a case in which rectangular pulses of a wide frequency range which are effective against unevenness of magnetostatic fields are transmitted as RF pulses, but possible cases are not limited to this.

Furthermore, when velocity encoding gradient pulses are to be transmitted as preparation pulses for instance, they may be transmitted on any desired plurality of axes. They may also be transmitted in any desired area. Besides that, they may also be transmitted in any desired number of times.

Further regarding the imaging sequence for instance, various techniques other than the SSFP method, that is, such as the FSE (fast spin echo), SE (spin echo), GRE (gradient recalled echo) and SPGR (spoiled GRASS) methods are available.

Also for instance, in the above-described modes for implementation, the scanning unit 2 transmits successively to the subject SU the first RF pulse RF1, the velocity encoding gradient pulse Gv and the second RF pulse RF2 so as to equalize the first time interval $\tau 1$ between the central time point tr1 of the time during which the first RF pulse RF1 is transmitted and the central time point tv of the time during which the velocity encoding gradient pulse Gv is transmitted and the second time interval $\tau 2$ between the central time point tv of the time during which the velocity encoding gradient pulse Gv is transmitted and the central time point tr2 of the time during which the second RF pulse RF2 is transmitted, but the possibility is not limited to this. Further in the above-described modes for implementation, the scanning unit 2 transmits the third RF pulse to the subject SU such that the central time point tr3 of the time during which this third RF pulse R3 is transmitted is within the first time interval $\tau 1$ between the central time point tr1 of the time during which the first RF pulse RF1 is transmitted and the central time point tv of the time during which the velocity encoding gradient pulse Gv is transmitted and matches the central time point $\tau c1$ of that first time interval $\tau 1$, but the possibility is not limited to this. Further in the above-described modes for implementation, the scanning unit 2 transmits the fourth RF pulse RF4 to the subject SU such that the central time point tr4 of the time during which this fourth RF pulse R4 is transmitted is within the second time interval $\tau 2$ between the central time point tv of the time during which the velocity encoding gradient pulse Gv is transmitted and the central time point tr2 of the time during which the second RF pulse RF2 is transmitted is within the second time interval $\tau 2$ and matches the central time point the central time point (c2 of the second time interval $\tau 2$, but the possibility is not limited to this. Elsewhere than at the timings of transmitting various pulses stated above, similar effects can be achieved. Incidentally, the prescription of the timings of transmitting various pulses as stated above can help reduce the duration of executing the preparation sequence, versatility can be enhanced.

The images of the imaging areas in the diastole and the systole may be generated by performing scans consisting of the preparation sequence PS and the imaging sequence IS, and MRA images regarding the imaging areas obtained on the basis of the difference value between those images as in the FBI process. Thus, a first image is generated by collecting imaging data in the imaging sequence IS after so applying preparation pulses in the preparation sequence PS as to vary the signal intensity of magnetization at a specific flow velocity, and a second image is generated by collecting imaging data in the imaging sequence IS after so applying preparation pulses in the preparation sequence PS as to vary the signal intensity of magnetization at another specific flow velocity. After that, an MRA image may be generated by performing difference processing between the first image and the second image. Another possibility is to generate a first image by collecting imaging data in the imaging sequence IS after so applying preparation pulses in the preparation sequence PS as to vary the signal intensity of magnetization at a specific flow velocity, generate a second image by collecting imaging data in the imaging sequence IS without executing the preparation sequence PS, and perform difference processing between the first image and the second image to generate an MRA image.

Where the scan is to be executed in synchronism with the subject's breathing, this can be applied. Here, for instance, it is suitable to execute the scan in synchronism with the state of expiration or inspiration.

The invention may also be applied in the preparation sequence PS, besides the case of maintaining the signal intensity of magnetization at a specific flow velocity and attenuating signal intensities of all other magnetizations, to maintaining signal intensities of other magnetizations by attenuating signal intensities of all other magnetizations.

Many widely different embodiments of the invention may be configured without departing from the spirit and the scope of the present invention. It should be understood that the present invention is not limited to the specific embodiments described in the specification, except as defined in the appended claims.

The invention claimed is:

1. A magnetic resonance imaging apparatus configured to transmit radio-frequency (RF) pulses to a subject in a magnetostatic space, configured to execute an imaging sequence in which magnetic resonance signals generated in the subject are obtained as imaging data by transmitting gradient pulses to the subject to whom the RF pulses have been transmitted, and configured to generate an image of the subject on the basis of the imaging data obtained by the execution of the imaging sequence, said magnetic resonance imaging apparatus comprising:

a scanning device comprising a magnet unit and a gradient coil unit, said scanning device configured to execute said imaging sequence and configured to execute, before the execution of said imaging sequence, a preparation sequence in which preparation pulses are transmitted to the subject, wherein said preparation pulses comprise, in sequence:
  a first RF pulse to flip spins oriented in a magnetostatic direction in the subject along a first plane including said magnetostatic direction and a first direction orthogonal to said magnetostatic direction, said first RF pulse flips the spins by a first flip angle of 45°;
  a second RF pulse that flips the spins by a second flip angle of 180°;
  a velocity encoding gradient pulse to mutually shift, in the spins flipped by said first RF pulse and said second RF pulse, the phase of spins of a first velocity and the phase of spins of a second velocity different from said first velocity;
  a third RF pulse that flips the spins by a third flip angle of 180°;
  a fourth RF pulse that flips the spins by a fourth flip angle of 45°; and
  a killer pulse to generate a gradient magnetic field which extinguishes a transverse magnetization of the spins flipped by said fourth RF pulse; and
a control unit communicatively coupled to said scanning device and configured to control said scanning device to perform said preparation sequence.

2. The magnetic resonance imaging apparatus according to claim 1, wherein said preparation pulses further comprise a second killer pulse, wherein said scanning device is configured to transmit said second killer pulse before transmitting said first RF pulse to generate a gradient magnetic field which extinguishes the transverse magnetization of spins in the subject.

3. The magnetic resonance imaging apparatus according to claim 1, wherein said scanning device is configured to transmit said velocity encoding gradient pulse to achieve an inverse polarity on a time axis with the central time point at which said velocity encoding gradient pulse is transmitted being as a pivot.

4. The magnetic resonance imaging apparatus according to claim 1, wherein said scanning device is configured to transmit said first RF pulse, said second RF pulse, said third RF pulse, and said fourth RF pulse as rectangular pulses.

5. The magnetic resonance imaging apparatus according to claim 1, wherein said scanning device is configured to successively transmit said first RF pulse, said velocity encoding gradient pulse and said fourth RF pulse to the subject to equalize a first time interval between the central time point of the duration of transmission of said first RF pulse and the central time point of the duration of transmission of said velocity encoding gradient pulse and a second time interval between the central time point of the duration of transmission of said velocity encoding gradient pulse and the central time point of the duration of transmission of said fourth RF pulse.

6. The magnetic resonance imaging apparatus according to claim 1, wherein:
  said scanning device is configured to successively transmit said first RF pulse, said velocity encoding gradient pulse and said fourth RF pulse to the subject to equalize a first time interval between the central time point of the duration of transmission of said first RF pulse and the central time point of the duration of transmission of said velocity encoding gradient pulse and a second time interval between the central time point of the duration of transmission of said velocity encoding gradient pulse and the central time point of the duration of transmission of said fourth RF pulse;
  said scanning device is configured to transmit said second RF pulse to the subject within said first time interval so that the central time point of said first time interval matches the central time point of the time during which said second RF pulse is transmitted; and
  said scanning device is configured to transmit said third RF pulse to the subject within said second time interval so that the central time point of said second time interval matches the central time point of the time during which said third RF pulse is transmitted.

7. The magnetic resonance imaging apparatus according to claim 1, wherein:
  said scanning device is configured to transmit said second RF pulse to flip the spins along a second plane containing said magnetostatic direction and a second direction orthogonal to said magnetostatic direction and said first direction; and
  said scanning device is configured to transmit said third RF pulse to flip the spins along said second plane.

8. The magnetic resonance imaging apparatus according to claim 1, wherein said scanning device is configured to transmit said velocity encoding gradient pulse to mutually shift the phase of the spins of said first velocity and the phase of the spins of said second velocity by an angle of 180°.

9. The magnetic resonance imaging apparatus according to claim 1, wherein said scanning device is configured to transmit said velocity encoding a slice selecting direction, a phase encoding direction and a frequency encoding direction.

10. The magnetic resonance imaging apparatus according to claim 1, wherein said scanning device is configured to transmit to the subject as said imaging sequence RF pulses in such a time of repeat that the longitudinal magnetization and the transverse magnetization of spins take on a steady state in the subject, and configured to apply to the subject as said gradient pulses a slice selecting gradient pulse to select a slice of the subject excited by said imaging sequence RF pulses, a phase encoding gradient pulse to phase-encode magnetic resonance signals generated in said slice excited by said imaging sequence RF pulses, and a frequency encoding gradient pulse to frequency-encode the magnetic resonance signals generated in said slice excited by said imaging sequence RF pulses such that the time-integrated value within said time of repeat is reduced to zero.

11. The magnetic resonance imaging apparatus according to claim 1, further comprising:
  an image generating device configured to generate images of the subject on the basis of said imaging data, wherein said image generating device comprises a computer; and
  a display device configured to display said images generated by said image generating device.

12. The magnetic resonance imaging apparatus according to claim 1, wherein said scanning device is configured to transmit said velocity encoding gradient pulse to mutually shift the phase of spins of which said first velocity is zero and the phase of spins which move at said second velocity.

13. The magnetic resonance imaging apparatus according to claim 1, wherein said scanning device is configured to execute a preparation sequence in the systole in heart beating of the subject and execute an imaging sequence in the diastole of said heart beating.

14. A magnetic resonance imaging apparatus configured to transmit radio-frequency (RF) pulses to a subject in a magnetostatic space, configured to execute an imaging sequence in which magnetic resonance signals generated in the subject are obtained as imaging data by transmitting gradient pulses to the subject to whom the RF pulses have been transmitted, and configured to generate an image of the subject on the basis of the imaging data obtained by the execution of the imaging sequence, said magnetic resonance imaging apparatus comprising:

a scanning device comprising a magnet unit and a gradient coil unit, said scanning device configured to execute the imaging sequence and configured to execute, before the execution of the imaging sequence, a preparation sequence in which preparation pulses are transmitted to the subject, wherein said preparation pulses comprise, in sequence:

a first RF pulse to flip spins oriented in a magnetostatic direction in the subject along a first plane including the magnetostatic direction and a first direction orthogonal to the magnetostatic direction, said first RF pulse flips the spins by a first flip angle of 45°;

a velocity encoding gradient pulse to mutually shift by an angle of 180°, in the spins flipped by said first RF pulse, the phase of spins of a first velocity and the phase of spins of a second velocity different from the first velocity;

a second RF pulse that flips the spins by a second flip angle of 45° and a killer pulse to generate a gradient magnetic field which extinguishes a transverse magnetization of the spins flipped by said second RF pulse; and a control unit communicatively coupled to said scanning device and configured to control said scanning device to perform said preparation sequence.

* * * * *

UNITED STATES PATENT AND TRADEMARK OFFICE
CERTIFICATE OF CORRECTION

Page 1 of 1

PATENT NO. : 9,014,782 B2
APPLICATION NO. : 11/612614
DATED : April 21, 2015
INVENTOR(S) : Miyoshi It is certified that error appears in the above-identified patent and that said Letters Patent is hereby corrected as shown below:

Specification

In Column 3, Lines 14-15, delete "FIGS. 8A1, 8A2, 8A3, 8A4, 8A5, 8B1, 8B2, 8B3, 8B4, and 8B5 are" and insert -- FIGS. 8A6, 8A7, 8A8, 8A9, 8B6, 8B7, 8B8, and 8B9 are --, therefor.

Claims

In Column 30, Line 27, in Claim 9, delete "encoding" and insert -- encoding gradient pulse in at least one of --, therefor.

Signed and Sealed this
Twelfth Day of January, 2016

Michelle K. Lee
*Director of the United States Patent and Trademark Office*